United States Patent  [19]

Nakamura et al.

[11] Patent Number: 5,098,600
[45] Date of Patent: Mar. 24, 1992

[54] LIQUID CRYSTAL COMPOUND, LIQUID CRYSTAL COMPOSITE INCLUDING THE COMPOUND AND LIQUID CRYSTAL DEVICE UTILIZING THE COMPOSITE

[75] Inventors: Shinichi Nakamura; Yoko Yamada, both of Atsugi; Hiroyuki Nohira, Urawa; Takao Takiguchi, Tokyo; Takashi Iwaki, Isehara; Takeshi Togano, Yokohama, all of Japan

[73] Assignee: Canon Kabushiki Kaisha, Tokyo, Japan

[21] Appl. No.: 630,845

[22] Filed: Dec. 20, 1990

[30] Foreign Application Priority Data

Dec. 22, 1989 [JP] Japan ................................. 1-333160

[51] Int. Cl.$^5$ ...................... C09K 19/34; C09K 19/52; C07D 285/12
[52] U.S. Cl. .......................... 252/299.61; 252/299.01; 252/299.63; 548/136
[58] Field of Search ...................... 252/299.61, 299.01; 548/136

[56] References Cited

U.S. PATENT DOCUMENTS

| | | | |
|---|---|---|---|
| 4,613,209 | 9/1986 | Goodby et al. | 350/350 S |
| 4,874,544 | 10/1989 | Yong et al. | 252/299.61 |
| 4,917,817 | 4/1990 | Nohira et al. | 252/299.01 |
| 4,918,213 | 4/1990 | Nohira et al. | 558/271 |
| 4,921,632 | 5/1990 | Nakamura et al. | 252/299.1 |
| 4,952,699 | 8/1990 | Yong et al. | 548/136 |
| 5,034,151 | 7/1991 | Shinjo et al. | 252/299.61 |

FOREIGN PATENT DOCUMENTS

| | | | |
|---|---|---|---|
| 0335348 | 10/1989 | European Pat. Off. | 548/136 |
| 3834926 | 4/1990 | Fed. Rep. of Germany | 548/136 |
| 0107216 | 8/1981 | Japan . | |

Primary Examiner—Robert L. Stoll
Assistant Examiner—C. Harris
Attorney, Agent, or Firm—Fitzpatrick, Cella, Harper & Scinto

[57] ABSTRACT

There is provided a liquid crystal compound represented by the following general formula (I), a liquid crystal composite including at least one kind of above liquid crystal compound and a liquid crystal device in which the liquid crystal composite is disposed between a pair of electrode substrates.

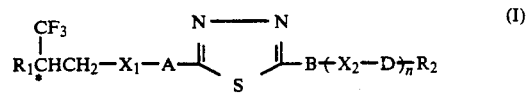

(I)

In the above formula (I), $R_1$ is a straight chain alkyl having 1-12 carbon atoms. $R_2$ is a straight chain or branched chain alkyl, which may have a substituted radical, having 1-18 carbon atoms and in which one or more than two methylene, which do not adjoin, may be substituted by —Y—,

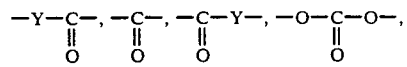

—CH=CH—, or —C|C—. Y is O or S. A is —A$_1$— or —A$_1$—A$_2$—, and B is —B$_1$— or —B$_1$—B$_2$—. A$_1$, A$_2$, B$_1$, and B$_2$ each is selected from

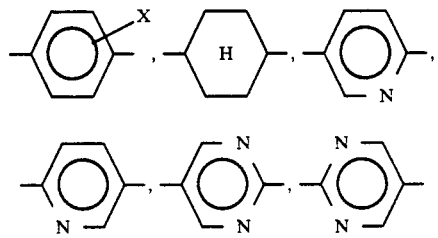

and a single bond. Z is hydrogen, halogen, cyano or methyl. X$_1$ is a single bond when A is a single bond and is —CH$_2$O—,

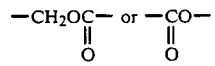

in other cases. n is 0 or 1,

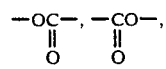

—OCH$_2$— or —CH$_2$O, and D is a single bond,

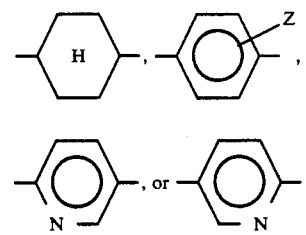

and *designates an asymmetric carbon atom.

22 Claims, No Drawings

LIQUID CRYSTAL COMPOUND, LIQUID CRYSTAL COMPOSITE INCLUDING THE COMPOUND AND LIQUID CRYSTAL DEVICE UTILIZING THE COMPOSITE

BACKGROUND OF THE INVENTION

1. Field of the Invention

The present invention relates to a new liquid crystal compound, a liquid crystal composite including the compound and a liquid crystal device utilizing the composite, and more particularly to a new liquid crystal composite having improved responsive characteristic to an electric field and a liquid crystal device utilizing the composite and for use in a liquid crystal display device, a liquid crystal-light shutter and the like which use the composite.

2. Description of the Prior Art

A liquid crystal has been conventionally applied to various kinds of fields as an electro-optic device. Most liquid crystals which are in practical use at present use Twisted Nematic (TN) liquid crystals, which are described in, for example, M. Schadt and W. Helfrich, "Voltage Dependent Optical Activity of a Twisted Nematic Liquid Crystal", Applied Physics Letters, Vol 18, No.4 (Feb. 15, 1971), pp.127-128.

These devices are based on dielectric alignment effects of the liquid crystal, in which by virtue of dielectric anisotropy, the average molecular long axis takes up a preferred orientation in an applied electric field. It is said that the minimum unit usable for the optical response speed of these devices is a millisecond, and this speed is too low for many potential applications. On the other hand, a simple matrix drive method is the most advantageous for an application of the liquid crystal to a wide flat display in consideration of price, productivity and so on. In the simple matrix method, scanning electrodes and signal electrodes are structured in a matrix. In order to drive the electrodes, a time-sharing drive method is adopted in which address signals are selectively applied to the scanning electrodes sequentially and cyclically, and predetermined information signals are selectively applied to the signal electrodes in parallel and in synchronization with the address signals.

However, when the above TN liquid crystal is applied to a device used in such a drive method, the electric field is finitely applied to a region where the scanning electrodes are selected and the signal electrodes are not selected, or a region where the scanning electrodes are not selected and the signal electrodes are selected (what is called a half-selected point).

If the difference between the voltage applied to the selected point and the voltage applied to the half-selected point is sufficiently large and a voltage threshold value required to align the liquid crystal molecules perpendicular to the electric field can be set at a voltage value between the voltage to the selected point and the half-selected point, the display device operates normally. However, as the number (N) of scanning lines is increased, the time (duty ratio) when an effective electric field is applied to one selected point during a scanning for an entire screen (1 frame) is decreased in the ratio of 1/N.

Therefore, when scanning operations are repeated, the difference as an effective value between the voltage to the selected point and the voltage to the non-selected point is increased as the number of scanning lines is increased. As a result, the lowering of an image contrast and cross talk are inevitable.

Such phenomena are substantially inevitable problems caused when a liquid crystal without bistability (its safe state is the state in which liquid crystal molecules are aligned horizontally to the electrode plane and the molecules are aligned perpendicularly only while the electric field is effectively applied) is driven by using the time cumulative effect (that is, when scanning operations are repeated).

Although the voltage averaging method, the dual frequency drive method, the multiplexing matrix method and so on have already been suggested in order to solve these problems, none of these methods is sufficient, and the improvements of a large screen and high density of display devices have reached the limit in the present since the number of scanning lines cannot be sufficiently increased.

In order to obviate such defects of a conventional liquid crystal device, the use of a liquid crystal device having bistability is suggested by Clark and Lagerwall (see Japanese Unexamined Patent No. 56-107216, U.S. Pat. No. 4,367,924 and so on).

As a bistable liquid crystal, a ferroelectric liquid crystal including a chiral smectic C phase (ScC* phase) or a H phase (SmH* phase) is used in general.

The ferroelectric liquid crystal has a bistable state which is composed of first and second optical stable states with respect to the electric field, and is different from the optical modulation device used in the above-mentioned TN liquid crystal. For example, the liquid crystal is aligned in the first optical stable state with respect to one electric field vector, and aligned in the second optical stable state with respect to the other electric field vector. Furthermore, this type of liquid crystal selects one of the above two stable states in response to the electric field to be applied and maintains the selected state when the electric field is not applied, that is, has bistability.

The ferroelectric liquid crystal has the excellent characteristic of having a high responsibility besides the bistability. This is because the spontaneous polarization, which the ferroelectric liquid crystal has, and the applied electric field directly operate to induce the transition of the alignment state, and the response speed of the ferroelectric liquid crystal is 3-4 orders higher than the response speed in the operation of the anisotropy of the dielectric constant and the electric field.

Thus, the ferroelectric liquid crystal latently has extremely excellent properties, and it is possible to essentially improve most of the above-described problems of the TN liquid crystal by utilizing such properties. In particular, applications of the ferroelectric liquid crystal to a high-speed optical shutter and a display on a wide screen with high density can be hoped. Although broad studies of liquid crystal materials having ferroelectricity have been made, it is difficult to say that the ferroelectric liquid crystal materials, which have been developed up to now, have sufficient properties including a low temperature operation property and a high-speed responsibility to be used in a liquid crystal device.

The relationship among the response time $\tau$, the amount Ps of the spontaneous polarization and the viscosity $\eta$ is shown by the following equation [II]:

$$\tau = \frac{\eta}{Ps \cdot E} \qquad [II]$$

(where E represents an applied electric field). Therefore, in order to increase the response speed, the following methods are used:
(a) to increase the amount Ps of the spontaneous polarization;
(b) to lower the viscosity $\eta$; and
(c) to decrease the applied electric field E.

However, since the drive is performed by an IC or the like, the applied electric field has the upper limit and is desirable to be as low as possible. Therefore, actually, it is necessary to lower the viscosity $\eta$ or to increase the amount Ps of the spontaneous polarization.

SUMMARY OF THE INVENTION

An object of the present invention is to provide a liquid crystal composite having a high response speed, in particular, a ferroelectric chiral smectic liquid crystal composite, and a liquid crystal device using the liquid crystal composite in order to put a ferroelectric liquid crystal device into practical use.

In other words, the object of the present invention is to provide a liquid crystal compound represented by the following general formula (I), a liquid crystal composite including at least one kind of liquid crystal compound and a liquid crystal device in which the liquid crystal composite is disposed between a pair of electrode substrates.

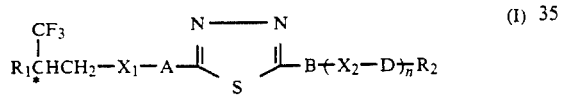

In the above formula (I), $R_1$ is a straight chain alkyl including 1-12 carbon atoms. $R_2$ is a straight chain or branched chain alkyl, which may have a substituted radical, including 1-18 carbon atoms and in which one or more than two methylene, which do not adjoin, may be substituted by —Y—,

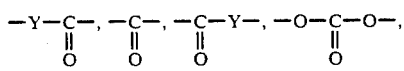

—CH=CH—, or —C≡C—. Y is O or S. A is —$A_1$— or —$A_1$—$A_2$—, and B is —$B_1$— or —$B_1$—$B_2$—. $A_1$, $A_2$, $B_1$ and $B_2$ each is selected from

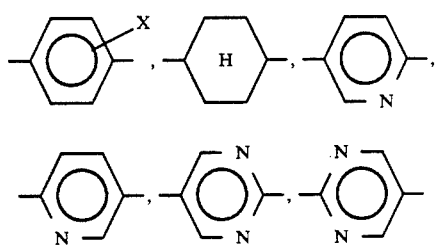

and a single bond. Z is hydrogen, halogen, cyano or methyl. $X_1$ is a single bond when A is a single bond and is —$CH_2O$—,

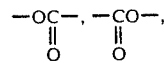

in other cases. n is 0 or 1, $X_2$ is

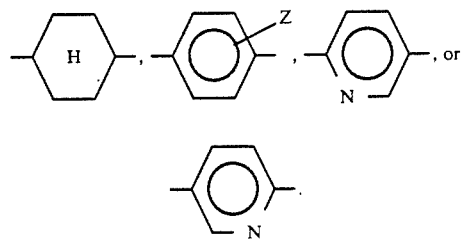

—$OCH_2$— or —$CH_2O$, and D is

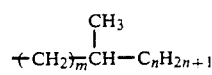

\* designates an asymmetric carbon atom.

DETAILED DESCRIPTION OF THE PREFERRED EMBODIMENTS

In the liquid crystal compound shown by the general formula (I), it is preferable that $R_2$ is selected from the following (i) to (iii):
i) a n-alkyl having 1 to 18 carbon atoms, and more preferably, 3 to 12 carbon atoms;
ii) a branched chain alkyl having the formula

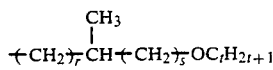

wherein m is one of integers of 0 to 7, and n is one of integers of 2 to 9, and this alkyl may be optically active.
iii) an alkyl ether having the formula $$\text{{CH}_2}_{\overline{r}}\overset{\overset{\text{CH}_3}{|}}{\text{CH}}\text{{CH}_2}_{\overline{s}}\text{OC}_t\text{H}_{2t+1}$$

where r is one of integers of 0 to 7 and s is 0 or 1. t is one of integers of 1 to 14, and this alkyl ether may be optically active.

Preferable structural formulas of the liquid crystal compound shown by the above general formula (I) are as follows.
i) When —A— is —A—, it is preferable that —$A_1$— is selected from a single bond,

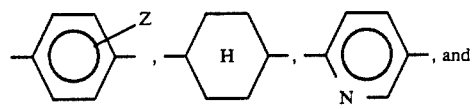

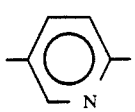

More preferably, it is selected from a single bond,

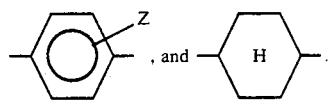

ii) When —A— is —A$_1$—A$_2$—, it is preferable that —A$_1$—A$_2$— is selected from

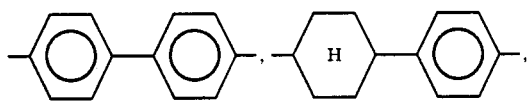

and

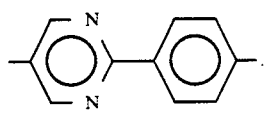

Furthermore, if —A$_1$— is a single bond in the above i), it is more preferable that —B— is selected from

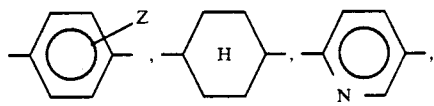

and if —A$_1$— is selected from

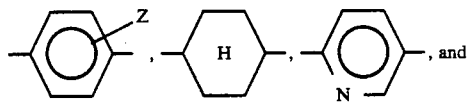

—B— is —B$_1$—, —B$_1$— is selected from a single bond,

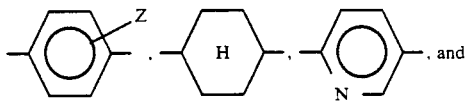

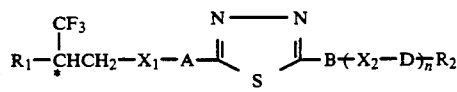

and more preferably from a single bond,

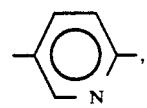

In the above ii), it is more preferable that —B— is a single bond.

Preferably, Z is hydrogen or halogen, and more preferably, hydrogen or fluorine.

A general method of synthesizing the liquid crystal compound shown by the above general formula (I) is as follows:

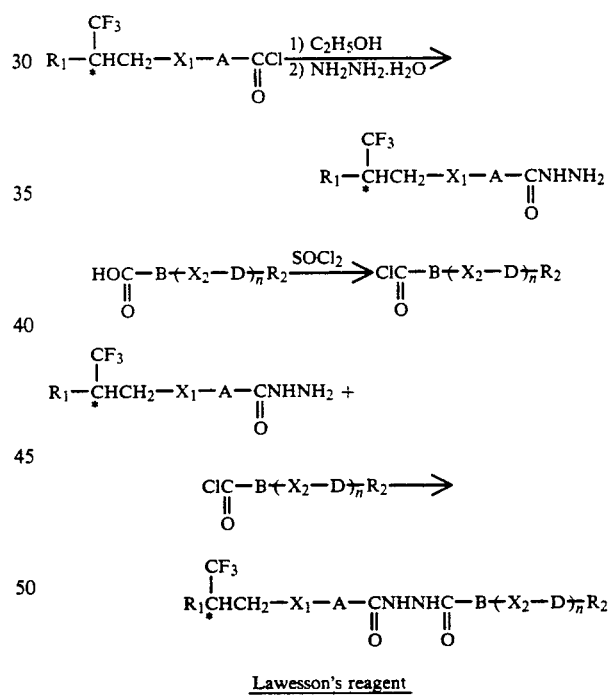

(R$_1$, R$_2$, X$_1$, X$_2$, A, B, D and n follow the definitions of the above general formula (I).)

If X$_1$ is not a single bond, if n is 1, or if n is 0 and methylene adjoining B in R$_2$ is substituted by

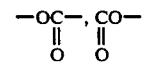

or the like, it is possible to protect a functional group in A or B by attaching a separable guard group, and to separate the guard group after the closing of the thiaziazole chain so that

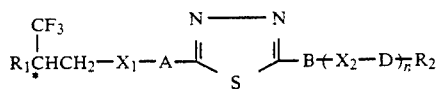

is obtained.

Preferably, the liquid crystal compound shown by the general formula is produced from an optically active 3-trifluoromethyl-1-alkane acid or 3-trifluoromethyl-1-alkanol shown by the following general formula (III), or the 3-trifluoromethyl-1-alkanol described in specifications of applications (Japanese Patent Applications Nos.62-183485 and 63-37624) by the applicant of the present invention.

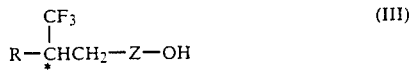  (III)

wherein R in the formula is alkyl in which the number of carbons is 1 to 12, Z is

or —CH$_2$—, and * designates an asymmetric carbon atom.

Specific structural formulas of the liquid crystal compound shown by the general formula (I) are as follows:

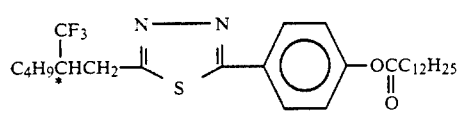 (1-1)

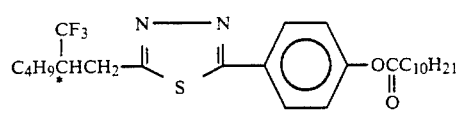 (1-2)

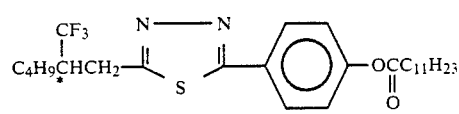 (1-3)

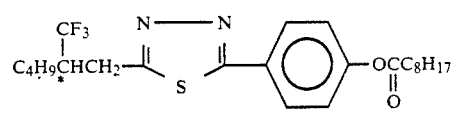 (1-4)

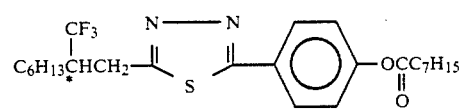 (1-5)

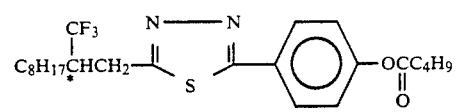 (1-6)

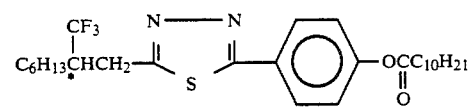 (1-7)

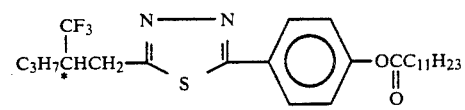 (1-8)

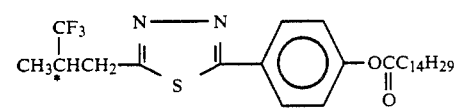 (1-9)

-continued
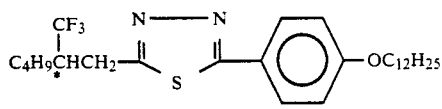 (1-10)
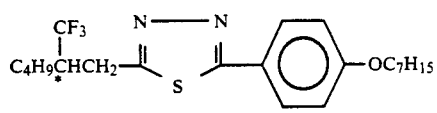 (1-11)
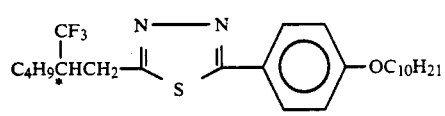 (1-12)
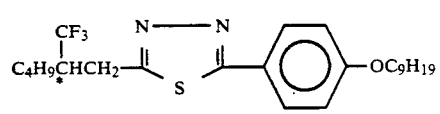 (1-13)
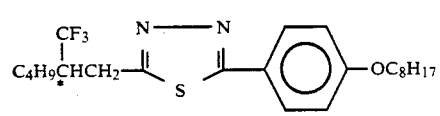 (1-14)
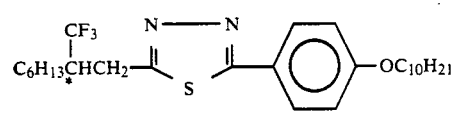 (1-15)
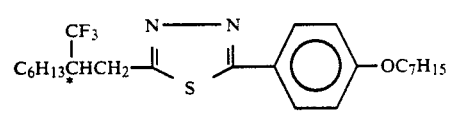 (1-16)
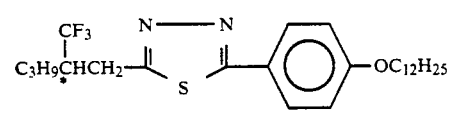 (1-17)
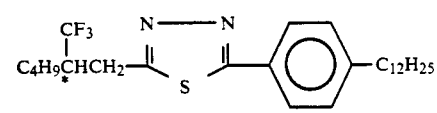 (1-18)
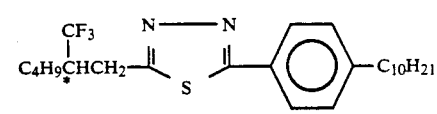 (1-19)
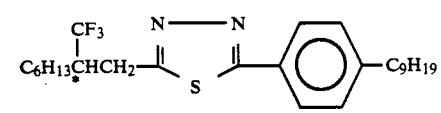 (1-20)
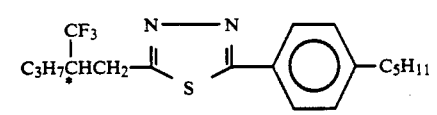 (1-21)
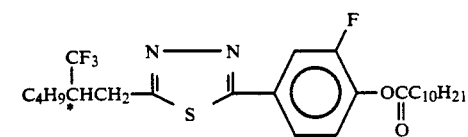 (1-22)

-continued
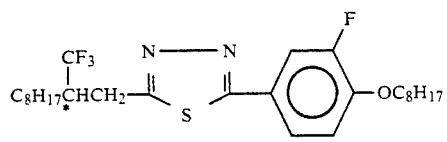 (1-23)
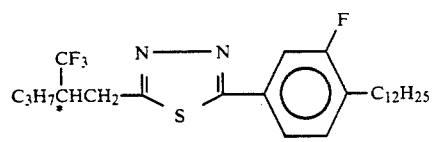 (1-24)
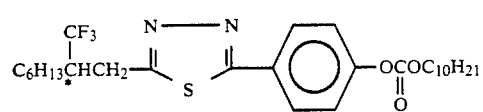 (1-25)
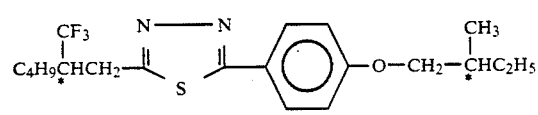 (1-26)
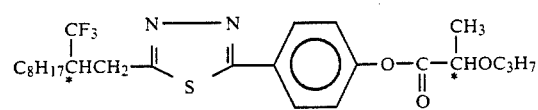 (1-27)
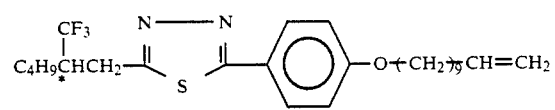 (1-28)
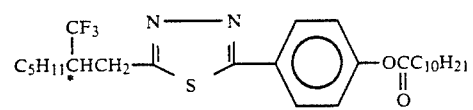 (1-29)
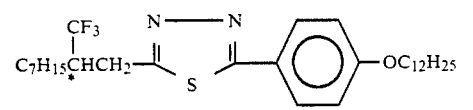 (1-30)
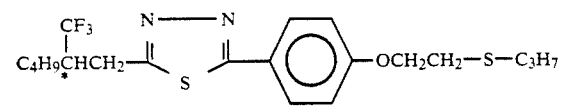 (1-31)
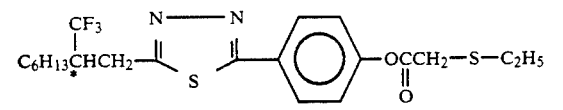 (1-32)
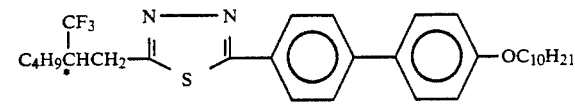 (1-33)
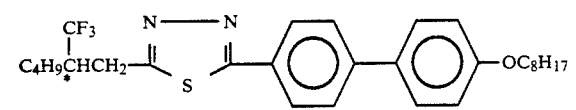 (1-34)
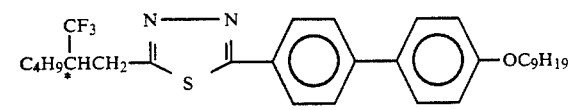 (1-35)

-continued
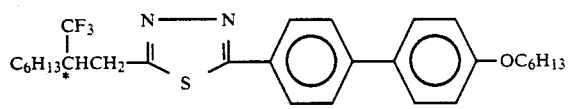
(1-36)
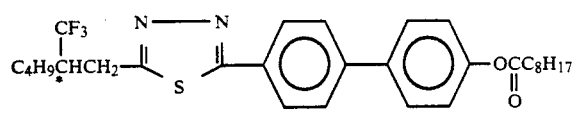
(1-37)
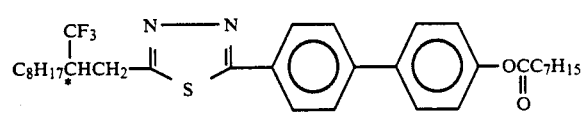
(1-38)
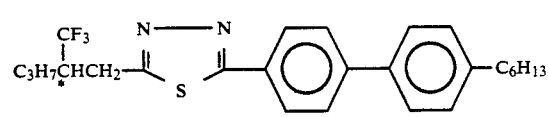
(1-39)
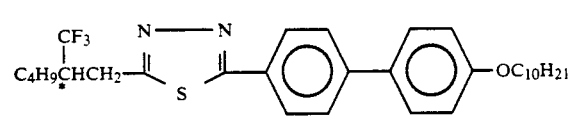
(1-40)
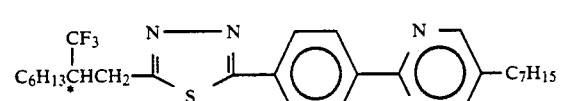
(1-41)
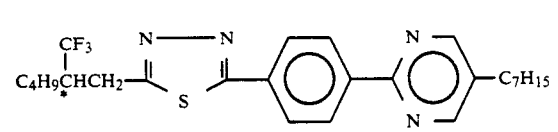
(1-42)
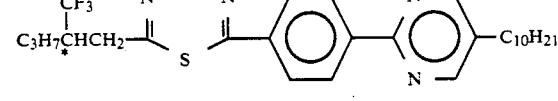
(1-43)
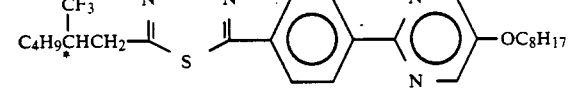
(1-44)
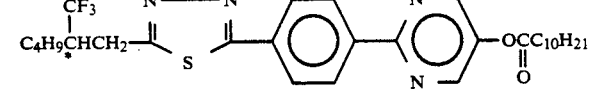
(1-45)
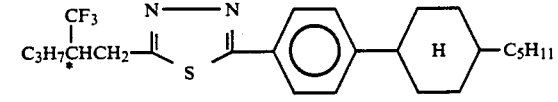
(1-46)
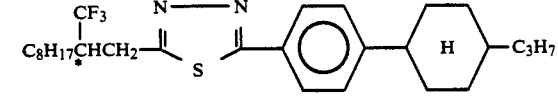
(1-47)
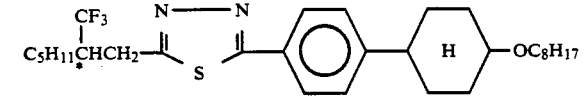
(1-48)

-continued
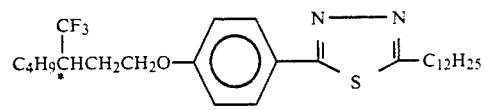 (1-49)
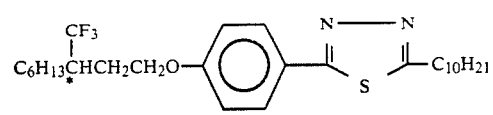 (1-50)
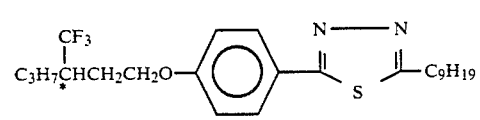 (1-51)
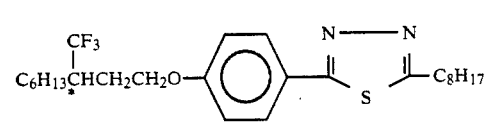 (1-52)
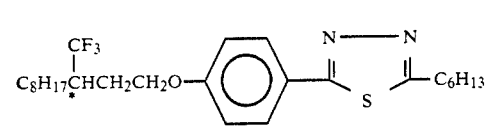 (1-53)
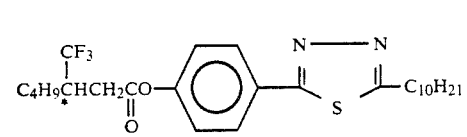 (1-54)
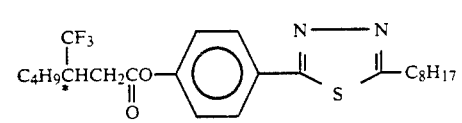 (1-55)
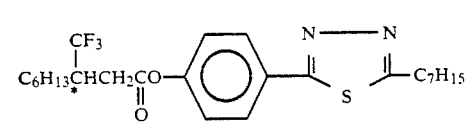 (1-56)
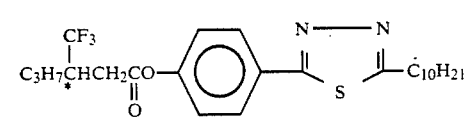 (1-57)
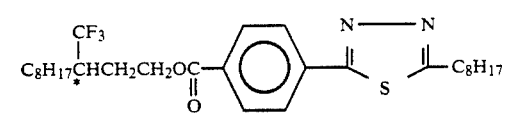 (1-58)
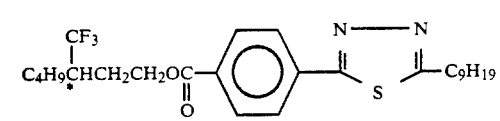 (1-59)
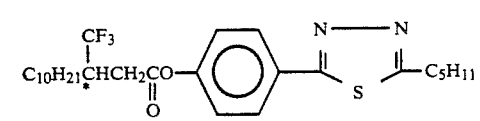 (1-60)
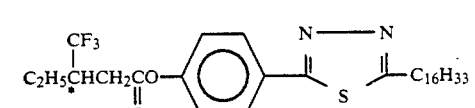 (1-61)

-continued
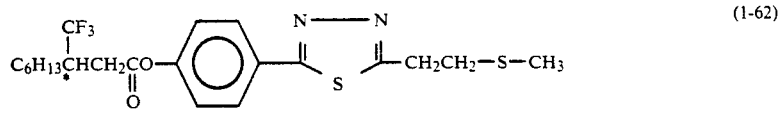 (1-62)
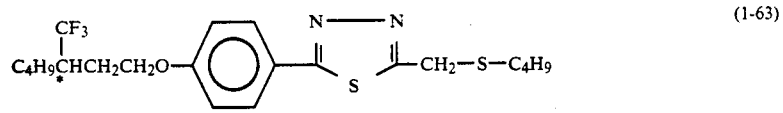 (1-63)
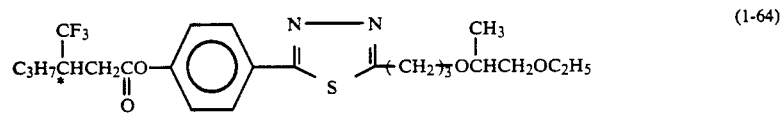 (1-64)
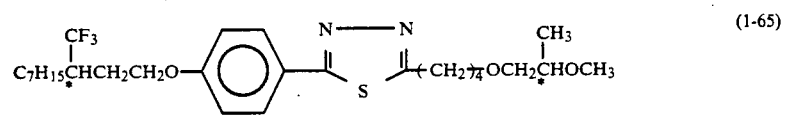 (1-65)
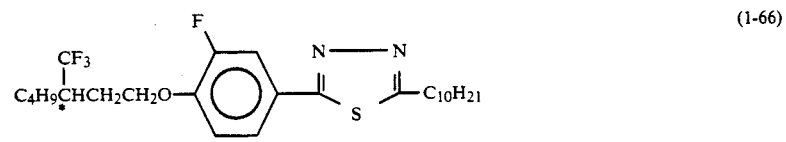 (1-66)
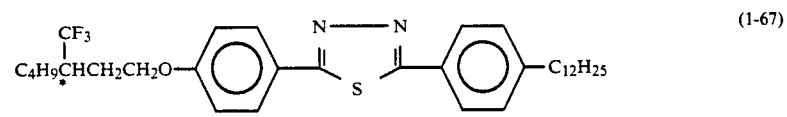 (1-67)
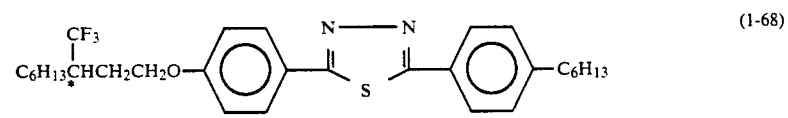 (1-68)
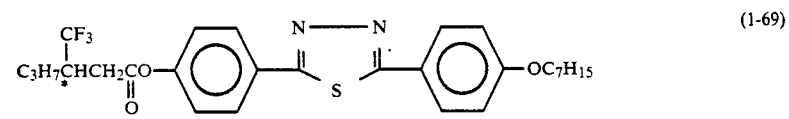 (1-69)
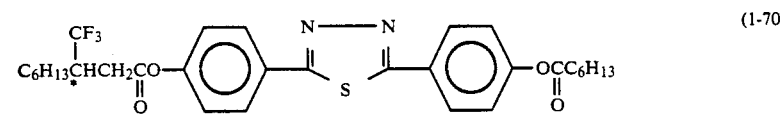 (1-70)
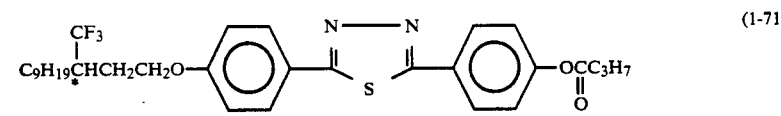 (1-71)
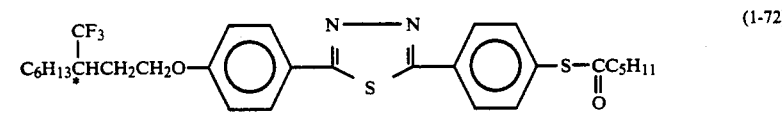 (1-72)
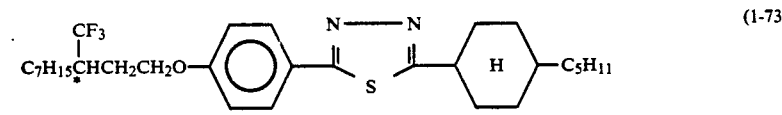 (1-73)
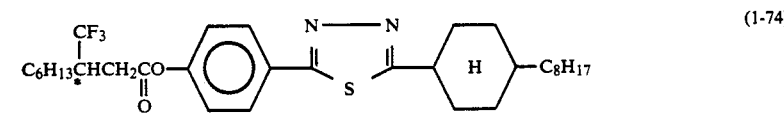 (1-74)

-continued
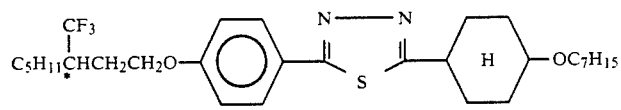 (1-75)
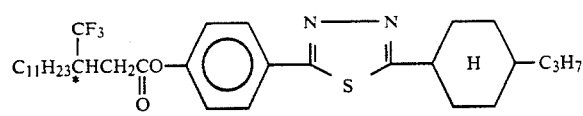 (1-76)
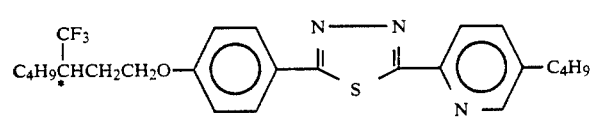 (1-77)
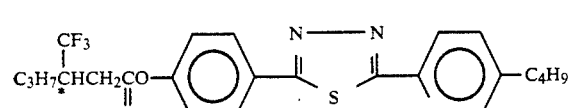 (1-78)
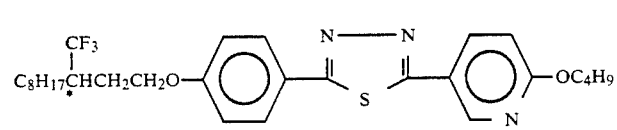 (1-79)
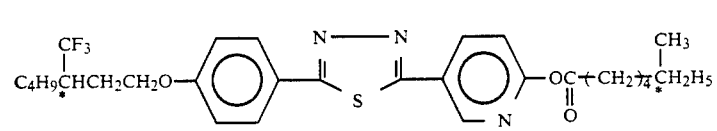 (1-80)
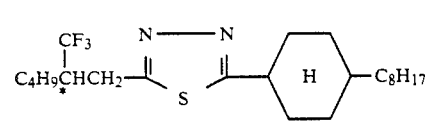 (1-81)
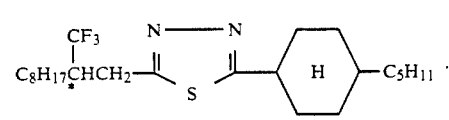 (1-82)
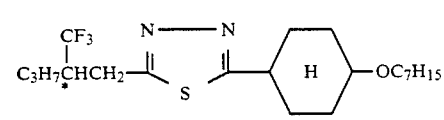 (1-83)
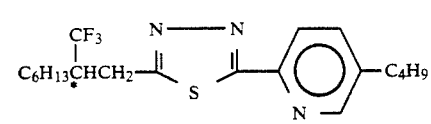 (1-84)
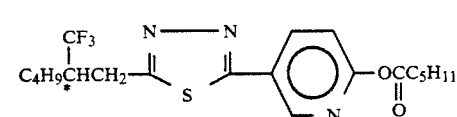 (1-85)
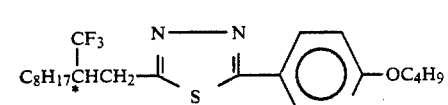 (1-86)
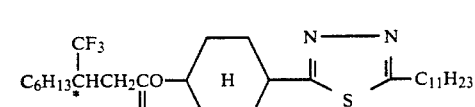 (1-87)

-continued
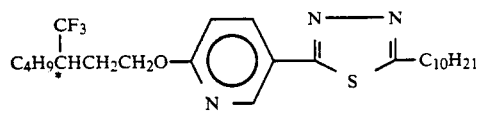 (1-88)
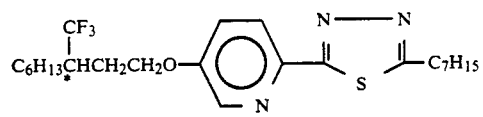 (1-89)
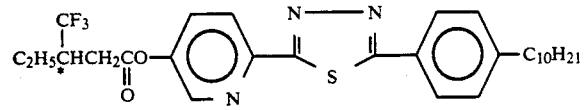 (1-90)
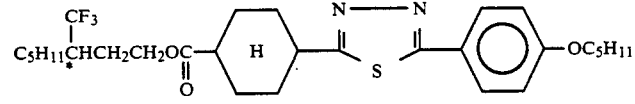 (1-91)
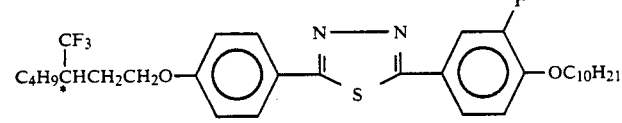 (1-92)
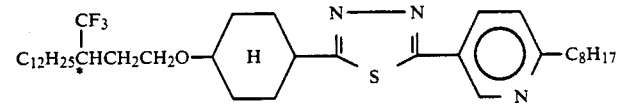 (1-93)
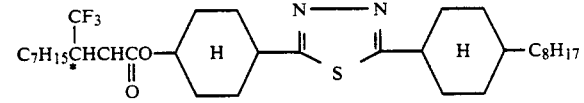 (1-94)
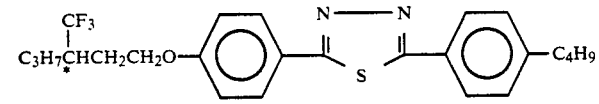 (1-95)
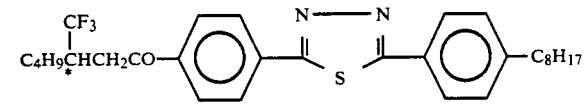 (1-96)
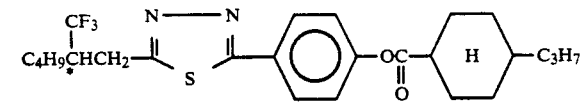 (1-97)
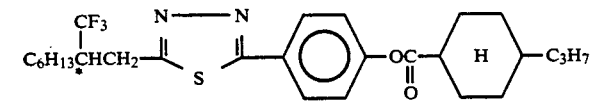 (1-98)
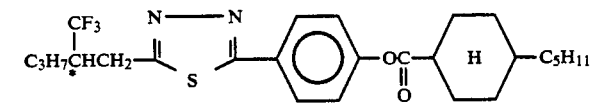 (1-99)
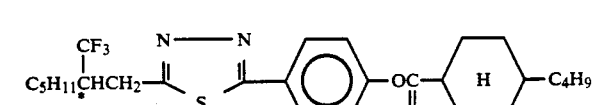 (1-100)

-continued

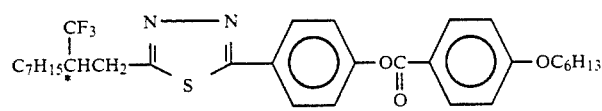
(1-101)

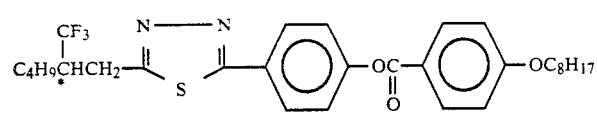
(1-102)

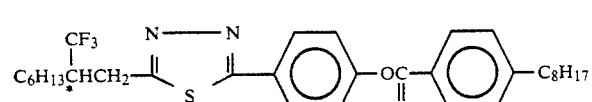
(1-103)

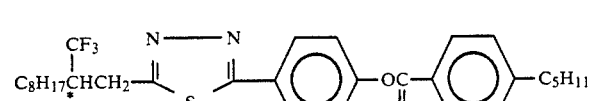
(1-104)

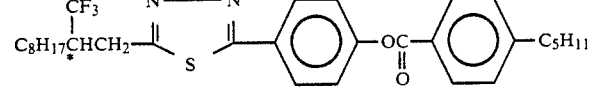
(1-105)

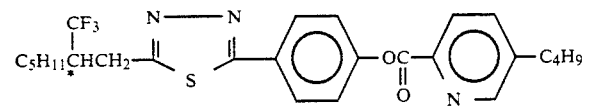
(1-106)

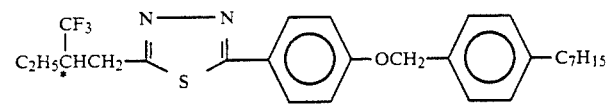
(1-107)

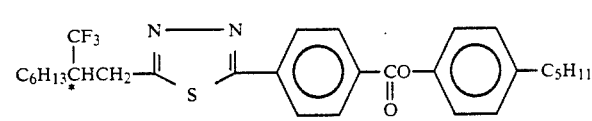
(1-108)

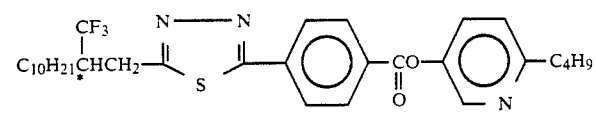
(1-109)

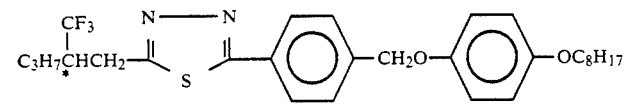
(1-110)

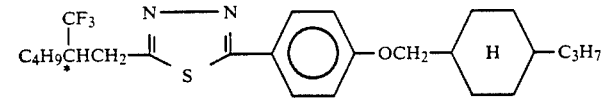

A liquid crystal composite according to the present invention contains at least one kind of optically active liquid crystal compound shown by the general formula (I) as a component thereof. For example, if the optically active liquid crystal compound is combined with ferroelectric liquid crystals having chiral smectic phases as shown by the following formulas (1) to (13), the spontaneous polarization is increased and the response speed can be improved.

In such an embodiment, it is preferable that the optically active liquid crystal compound of the present invention shown by the general formula (I) is used in a weight ratio of 0.1% to 99%, and more particularly, 1% to 90%, based on the total weight of a liquid crystal composite to be obtained.

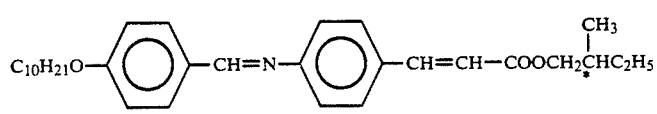
(1)

p-decyloxy-benzylidene-p'-amino-2-methylbutyl-cinnamate (DOBAMBC)

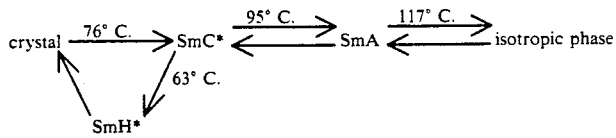
(2)
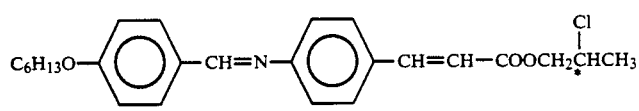
p-hexyloxy-benzilidene-p'-amino-2-chloropropyl-cinnamate (HOBACPC)
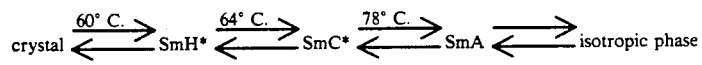
(3)
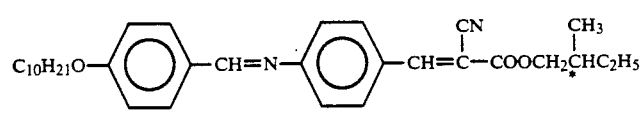
p-decyloxy-benzylidene-p'-amino-2-methylbutyl-α-cyanocinnamate (DOBAMBCC)
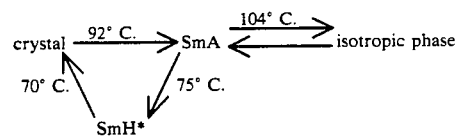
(4)
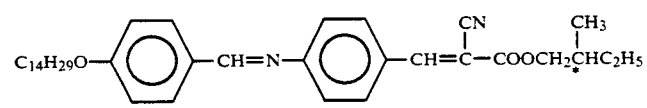
p-tetradecyloxy-benzylidene-p'-amino-2-methylbutyl-α-cyanocinnamate (TDOBAMBCC)
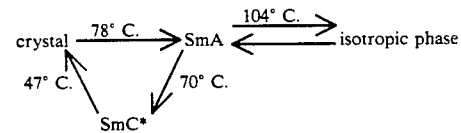
(5)
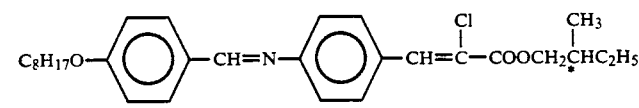
p-octyloxy-benzylidene-p'-amino-2-methylbutyl-α-chlorocinnamate (OOBAMBCC)
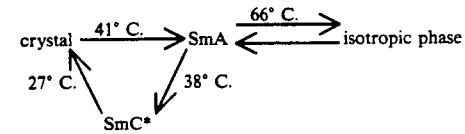
(6)
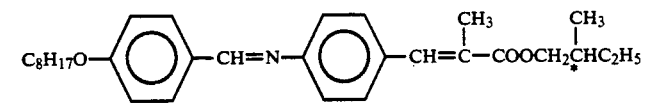
p-octyloxy-benzylidene-p'-amino-2-methylbutyl-α-methylcinnamate
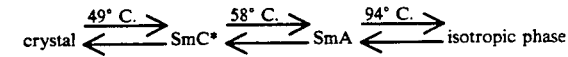

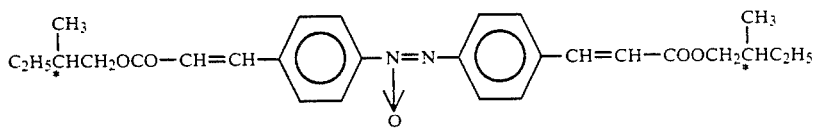

4,4'-azoxycinnamic acid-bis(2-methylbutyl)ester crystal $\underset{\longleftarrow}{\overset{121° C.}{\longrightarrow}}$ SmC* $\underset{\longleftarrow}{\overset{134° C.}{\longrightarrow}}$ SmA $\underset{\longleftarrow}{\overset{168° C.}{\longrightarrow}}$ isotropic phase (8)

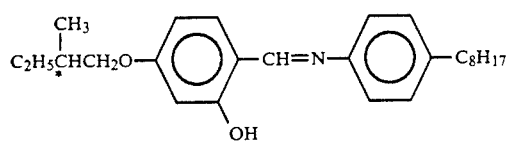

4-o-(2-methyl)-butyl-resorcylidene-4'-octylaniline (MBRA 8)

crystal $\underset{\longleftarrow}{\overset{28° C.}{\longrightarrow}}$ SmC* $\underset{\longleftarrow}{\overset{55° C.}{\longrightarrow}}$ SmA $\underset{\longleftarrow}{\overset{62° C.}{\longrightarrow}}$ isotropic phase (9)

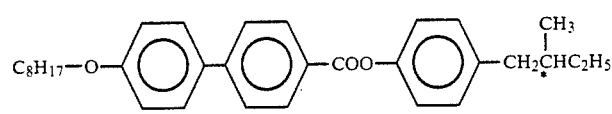

4-(2'-methylbutyl)phenyl 4'-octyloxybiphenyl-4-carboxylate crystal $\underset{\longleftarrow}{\overset{78° C.}{\longrightarrow}}$ Sm3 $\underset{\longleftarrow}{\overset{80° C.}{\longrightarrow}}$ SmC* $\underset{\longleftarrow}{\overset{128.3° C.}{\longrightarrow}}$ SmA $\underset{\longleftarrow}{\overset{171.0° C.}{\longrightarrow}}$ cholesteric phase $\underset{\longleftarrow}{\overset{174.2° C.}{\longrightarrow}}$ isotropic phase (10)

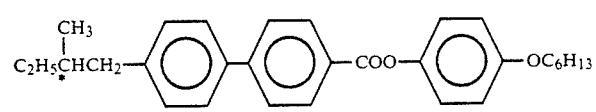

4-hexyloxyphenyl 4-(2''-methylbutyl)biphenyl-4'-carboxylate crystal $\underset{\longleftarrow}{\overset{68.8° C.}{\longrightarrow}}$ SmC* $\underset{\longleftarrow}{\overset{80.2° C.}{\longrightarrow}}$ cholesteric phase $\underset{\longleftarrow}{\overset{163.5° C.}{\longrightarrow}}$ isotropic phase (11)

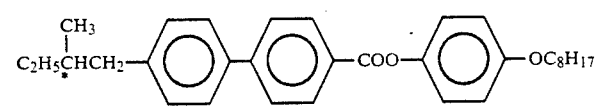

4-octyloxyphenyl 4-(2''-methylbutyl)biphenyl-4'-carboxylate crystal $\underset{\longleftarrow}{\overset{76° C.}{\longrightarrow}}$ SmC* $\underset{\longleftarrow}{\overset{88.6° C.}{\longrightarrow}}$ cholesteric phase $\underset{\longleftarrow}{\overset{155.4° C.}{\longrightarrow}}$ isotropic phase (12)

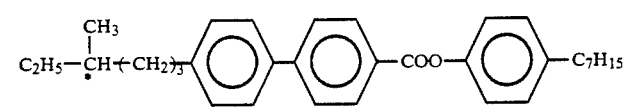

4-heptylphenyl 4-(4''-methylhexyl)biphenyl-4'-carboxylate crystal $\underset{\longleftarrow}{\overset{91.5° C.}{\longrightarrow}}$ SmC* $\underset{\longleftarrow}{\overset{93° C.}{\longrightarrow}}$ SmA $\underset{\longleftarrow}{\overset{112° C.}{\longrightarrow}}$ cholesteric phase $\underset{\longleftarrow}{\overset{131° C.}{\longrightarrow}}$ isotropic phase (13)

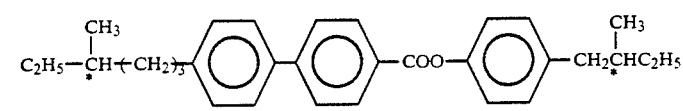

-continued 4-(2''-methylbutyl)phenyl 4-(4'''-methylhexyl)biphenyl-4'-carboxylate crystal $\xrightarrow{83.4° C.}$ cholesteric phase $\xrightarrow{114° C.}$ isotropic phase SmC* $\xleftarrow{74.3° C.}$ SmA 81.0° C.

In addition to the above compounds, the following liquid crystal compounds are also suitable for being combined with the optically active liquid crystal compound to form the liquid crystal composite according to the present invention.

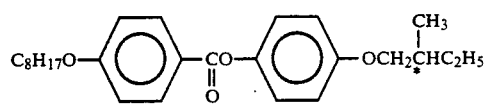

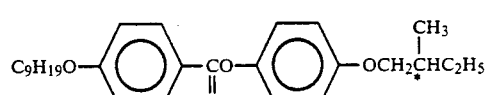

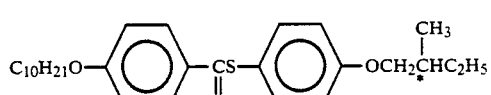

As a further embodiment, the liquid crystal composite capable of being used as a ferroelectric liquid crystal according to the present invention can be obtained by combining the optically active liquid crystal compound with non-chiral compounds, which are, however, smectic liquid crystals themselves.

In this embodiment, it is preferable that the optically active liquid crystal compound of the present invention shown by the general formula (I) forms 0.1% to 99%, in particular, 1% to 99% by weight of a liquid crystal composite to be obtained.

In such a composite, a large spontaneous polarization can be obtained in accordance with the amount of the optically active liquid crystal compound contained in the composite.

A list of such non-chiral smectic liquid crystal compounds is shown as follows:

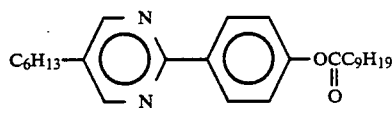

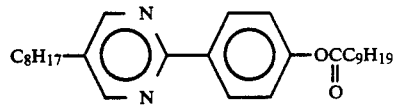

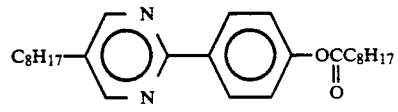

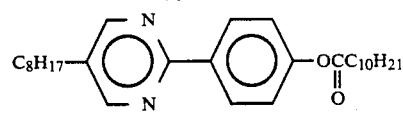

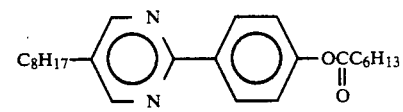

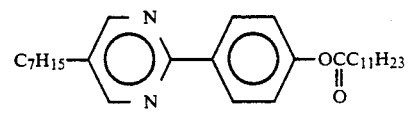

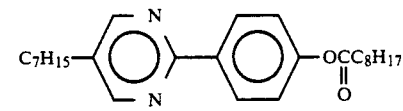

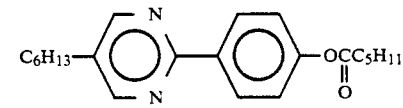

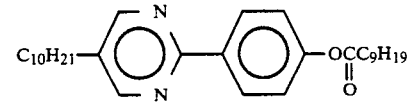

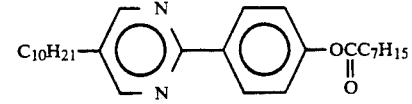

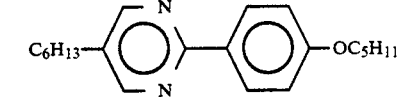

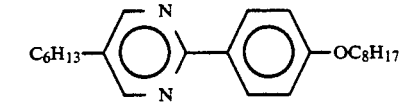

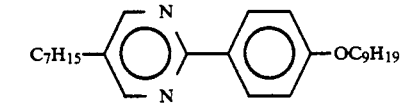

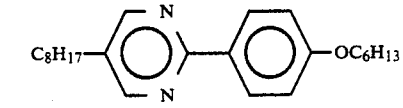

-continued
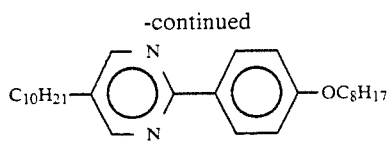
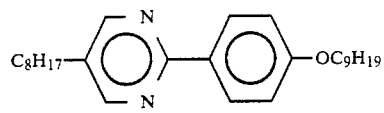
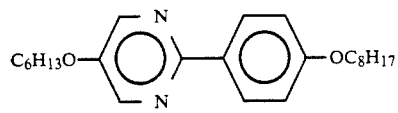
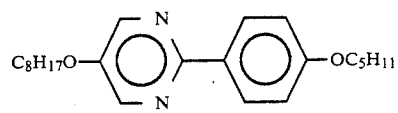
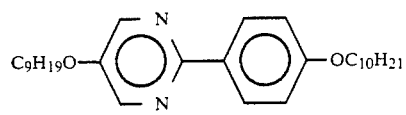
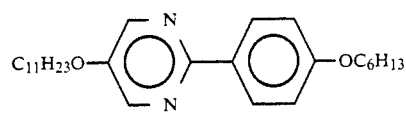
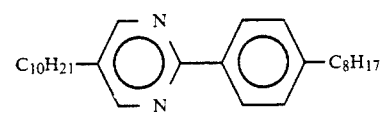
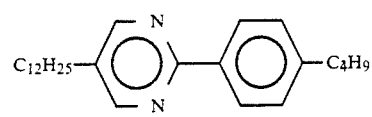
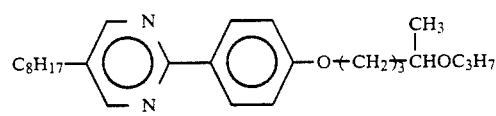
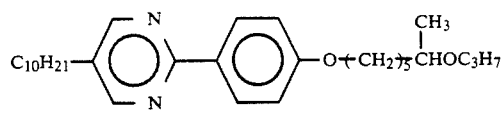
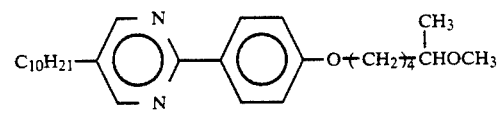
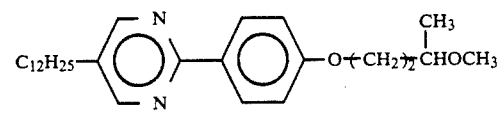
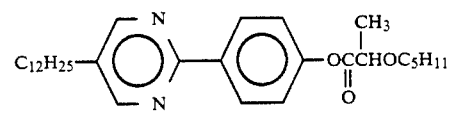
-continued
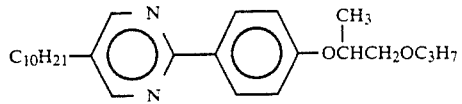
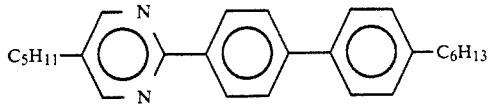
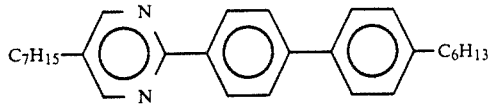
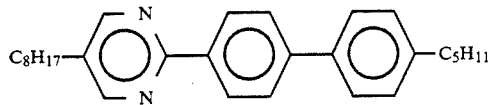
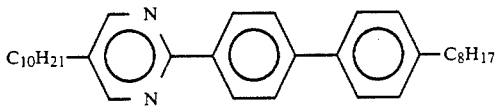
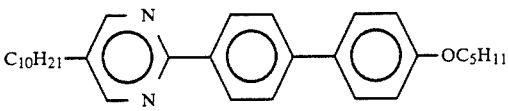
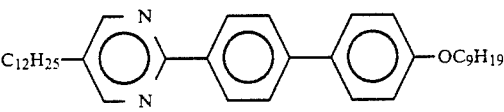
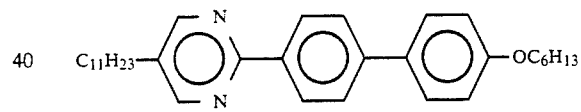
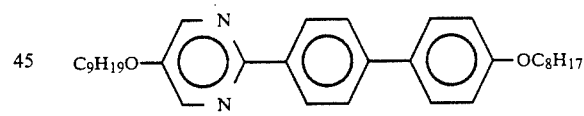
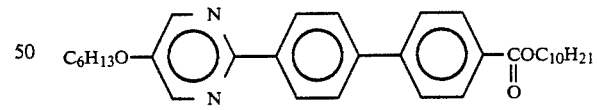
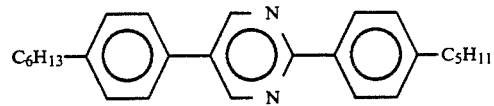
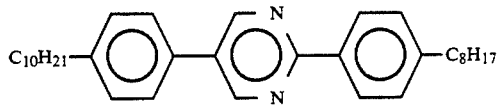
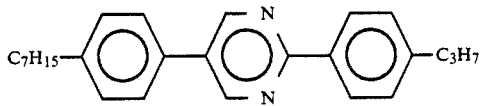

-continued
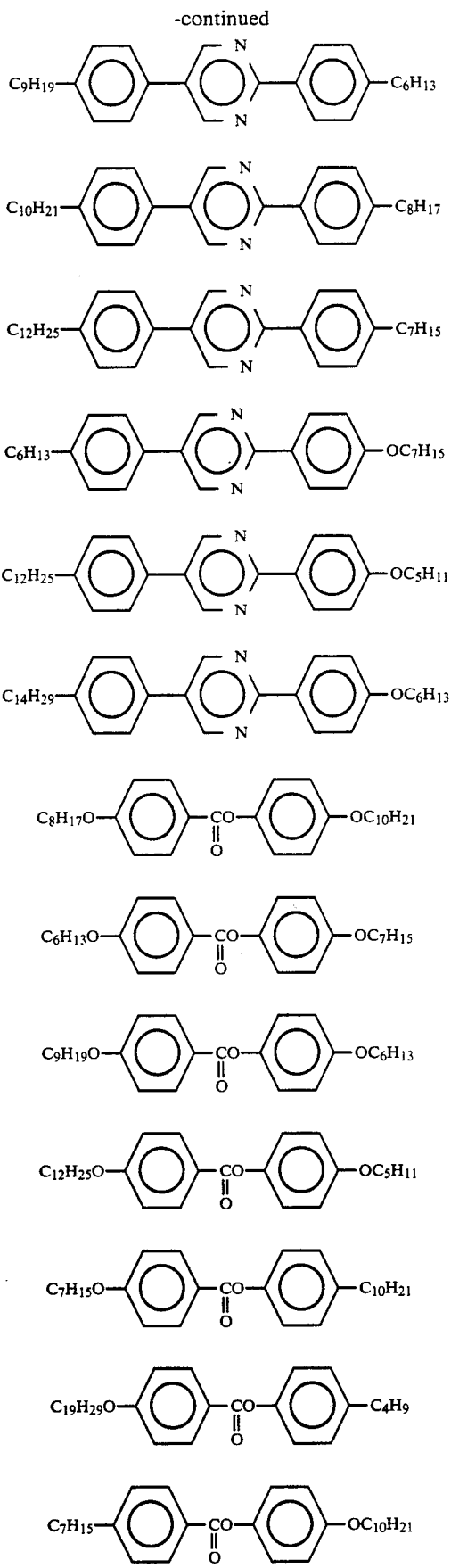
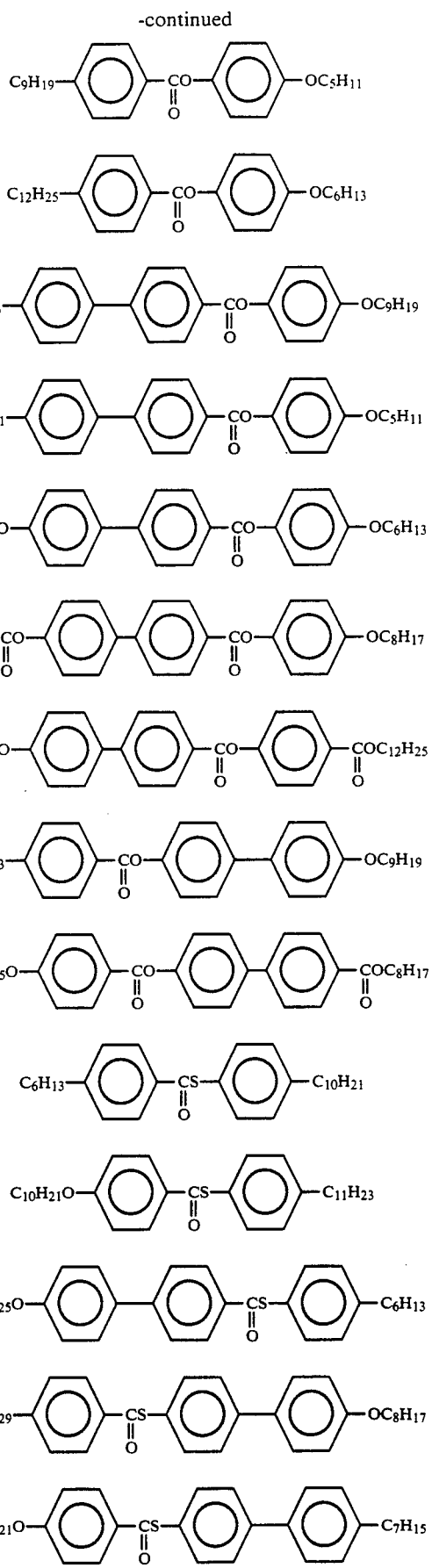

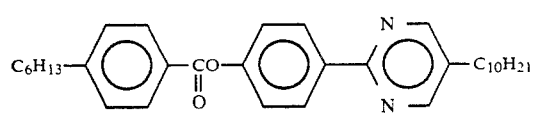
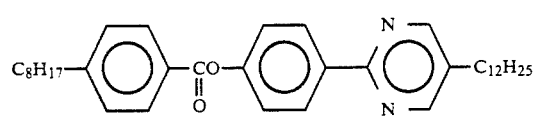
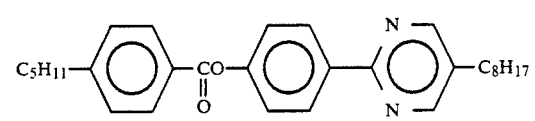
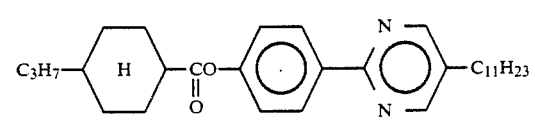
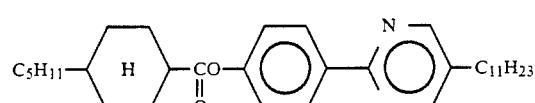
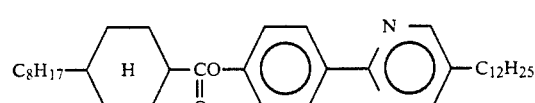
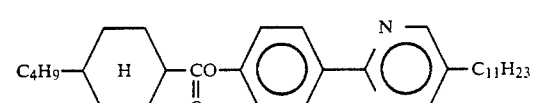
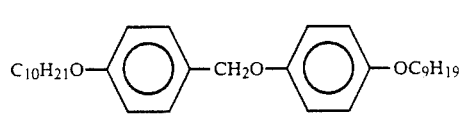
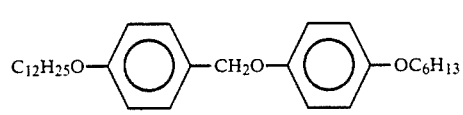
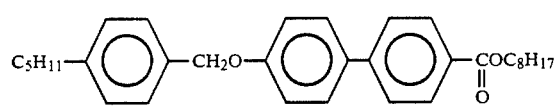
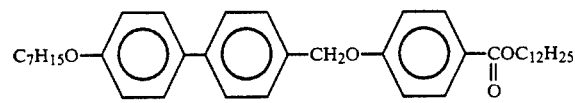
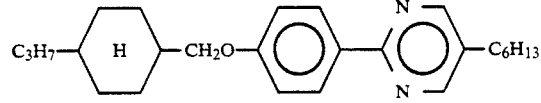
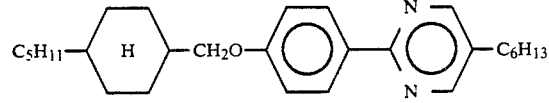
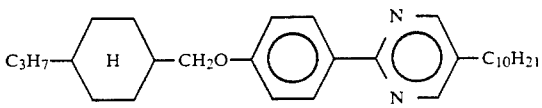
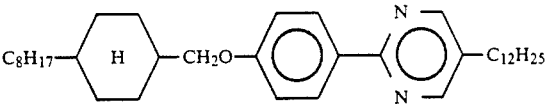

The optically active liquid crystal shown by the general formula (I) is effective in preventing reverse domain from being caused in a TN cell by being added to a nematic liquid crystal. In such embodiment, it is preferable that the optically active liquid crystal compound shown by the general formula (I) forms 0.01 to 50% by weight of a liquid crystal composite to be obtained.

Furthermore, by being added to a nematic liquid crystal or a chiral nematic liquid crystal, the optically active liquid crystal compound can be used in a phase transition liquid crystal device and a White Tailer guest-host liquid crystal device as a liquid crystal composite. In this case, it is preferable that the optically active liquid crystal compound shown by the formula (I) forms 0.01 to 80% by weight of a liquid crystal composite to be obtained.

The present invention will now be described more specifically with reference to the following embodiments.

EMBODIMENT 1

Production of 2-(2-trifluoromethylhexyl)-5-(4-undecanoyloxyphenyl)-1, 3, 4-thiadiazole (the illustrated compound 1-2)

According to the following steps, 2-(2-trifluoromethylhexyl)-5-(4-undecanoyloxyphenyl)-1, 3, 4-thiadiazole was produced.

Step 1)

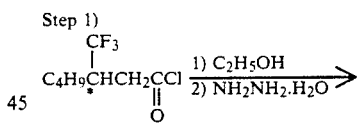

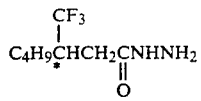

Step 2)

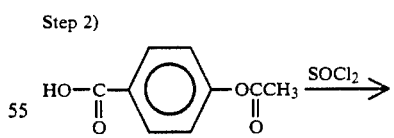

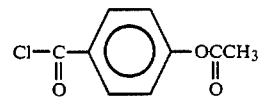

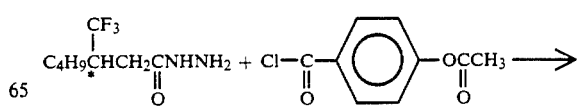

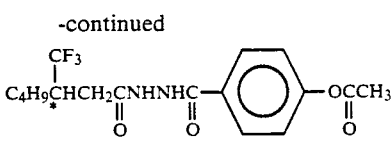

Step 3)

Lawesson's reagent →

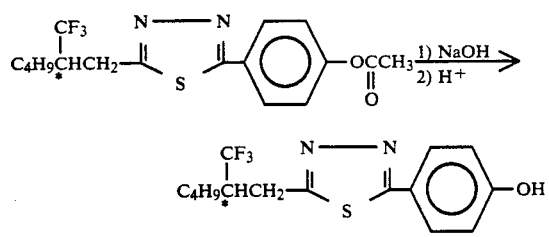

Step 4)

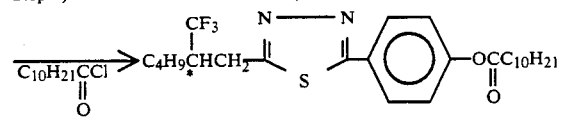

Step 1) Production of 2-trifluoromethylhexyl hydrazide 2.5 g (10 mmol) of 3-trifluorometylheptane chloride was dripped into 50 ml of ethanol and the mixture was heated at 80° C. for one hour. After that, 1.5 g (30 mmol) of hydrazine hydrate was added to the solution and the mixture was heated and refluxed for four hours. After the reaction was completed, 1.7 g (8.2 mmol) of 2-trifluoromethylhexyl hydrazide was obtained by adding 30 ml of iced water, cooling the solution, filtering the solution and cleaning deposited crystals by water and ethanol respectively.

2) Production of N-(2-trifluoromethylhexyl)-N'-4-acetoxybenzdihydrazide

After heating and refluxing 1.4 g (8.0 mmol) of 4-acetoxybenzoic acid and 6 ml of thionyl chloride, surplus thionyl chloride was removed, and 4-acetoxybenzoic acid chloride was obtained. Then, a mixed solution of 1.7 g of the hydrazide obtained in Step 1, 1 ml of pyridine and 15 ml of dioxane was added to the 4-acetoxybenzoic acid chloride and the mixture was heated and refluxed for two hours. After the reaction was completed, 2.6 g (7.0 mmol) of dihydrazide was obtained by pouring a 50 ml solution of salt, filtering and cleaning the crystals which had deposited, by water and methanol.

Step 3) Production of 2-(2-trifluoromethylhexyl)-5-(4-hydroxyphenyl)-1, 3, 4-thiadiazole 2.6 g (7.0 mmol) of the dihydrazide obtained in Step 2 and 2.9 g (7.1 mmol) of the Lawesson's reagent were added to 10 ml of tetrahydrofuran and the mixture was stirred at 70° C. for one hour. After the reaction was completed, a sodium hydrogencarbonate solution (5%) was added and ether extraction was performed. After removing the solvent, 20 ml of ethanol and 0.9 g (21 mmol) of sodium hydroxide (95%) were added and the mixture was stirred for one hour at room temperature. After removing the solvent, 3N-HCl was added so as to obtain a pH of 5 to 6, and then ether extraction was performed. Sodium sulfuric anydride was added to the extracted liquid, the mixture was dried, the solvent was removed, 1.0 g of a desired material was obtained by column chromatography (toluene) and recrystallizing (toluene/methanol) the obtained rough crystals.

Step 4) Production of 2-(2-trifluoromethylhexyl)-5-(4-undecanoyloxyphenyl)-1, 3, 4-thiadiazole 0.66 g (2 mmol) of 2-(2-trifluoromethylhexyl)-5-(4-hydroxyphenyl)-1, 3, 4-thiadiazole was added to pyridine, 0.50 g (2,5 mmol) of undecanoic acid chloride was dripped while the mixture was cooled, and they were stirred at 50° C. for two hours. After the reaction was completed, water was added, ether extraction was performed, the solution was dried, and the solvent thereof was removed. Then, the solution was refined by column chromatography (toluene: ethyl acetate=6:1) and recrystallization (ethanol), and 0.72 g of a desired material was obtained.

Phase transition temperature (°C.)

Cry ⇌ 52.4 / 32.4 ⇌ Iso.

EMBODIMENT 2

Production of 2-decyl-5-[4-(3-trifluoromethylheptanoloxy)phenyl]-1, 3, 4-thiadiazole (the illustrated compound 1-54)

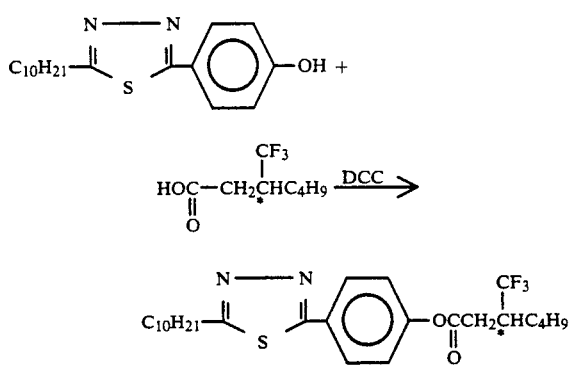

1.0 g of 2-decyl-5-(4-hydroxyphenyl)-1, 3, 4-thiadiazole, 0.67 g of 3-trifluoromethylheptanoic acid, 0.64 g of dicyclohexylcarbodiimide and 0.05 g of pyrrolidinopyridine were added to 5 ml of benzene and 10 ml of dichloromethane, and the mixture was stirred for twenty-four hours at room temperature. After the reaction was completed, the mixture was filtered so as to remove crystals and a filtrate was obtained. The solvent was removed, the filtrate was refined by column chromatography (benzene) and recrystallization (ethanol), and 1.0 g of a desired material was obtained.

Phase transition temperature (°C.)

Cry ⇌ 63.0 / 52.4 ⇌ Iso.

EMBODIMENT 3

Production of
2-decyl-5-[4-(3-trifluoromethylnonyloxy)phenyl]-1, 3, 4-thiadiazole (the illustrated compound 1-50)

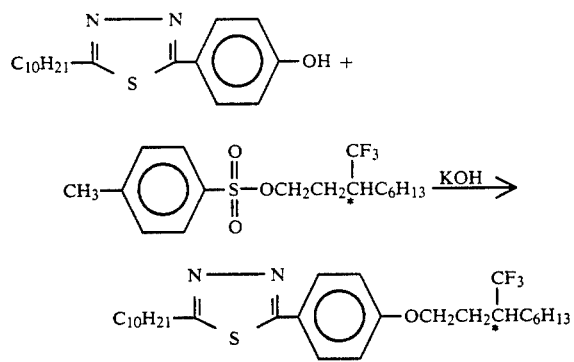

0.25 g of 2-decyl-5-(4-hydroxyphenyl)-1, 3, 4-thiadiazole, 0.23 g of p-toluenesulfonic acid 3-trifluoromethylnonyl, and 0.063 g of potassium hydroxide were added to 1 ml of dimethylformamide, and the mixture was stirred at 100° C. for six hours. After the reaction was completed, water was added, toluene extraction was performed, the solution was dried, the solvent was removed, and the solution was refined by column chromatography (toluene:ethyl acetate=10:1) and recrystallization (ethanol), so that 0.27 g of a desired material was obtained.

Phase transition temperature (°C.)

$$Cry \underset{38.5}{\overset{56.7}{\rightleftarrows}} Iso.$$

EMBODIMENT 4

Production of
2-(4-octylphenyl)-5-[4(3-trifluoromethylheptanoyloxy)-phenyl]-1, 3, 4-thiadiazole (the illustrated compound 1-96)

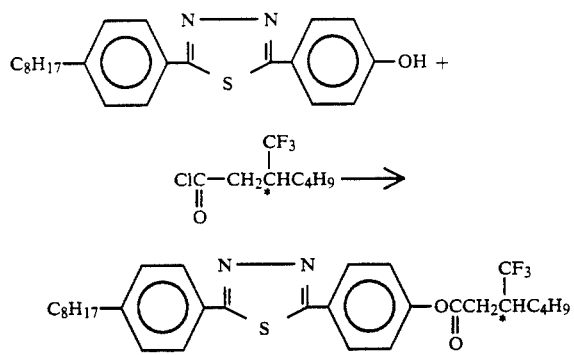

0.59 g of 2-(4-octylphenyl)-5-(4-hydroxyphenyl)-1, 3, 4-thiadiazole was added to pyridine, 0.35 g of 3-trifluoromethylheptaheptanoic acid chloride was dripped into the mixture which was being cooled by ice, and the mixture was stirred for twenty-four hours at room temperature. After the reaction was completed, water was added, ethyl acetate was extracted, the solution was dried, the solvent was removed, and the solution was refined by the column chromatography (toluene:ethyl acetate=3:1) and the recrystallization (toluene/ethanol), so that 0.60 g of the desired material was obtained.

Phase transition temperature (°C.)

$$Cry \underset{110.2}{\overset{113.5}{\rightleftarrows}} S_c* \underset{121.1}{\overset{122.7}{\rightleftarrows}} Iso.$$

EMBODIMENT 5

Production of
2-(4-hexylphenyl)-5-[4-(3-trifluoromethylnonyloxy)-phenyl]-1, 3, 4-thiadiazole (the illustrated compound 1-68)

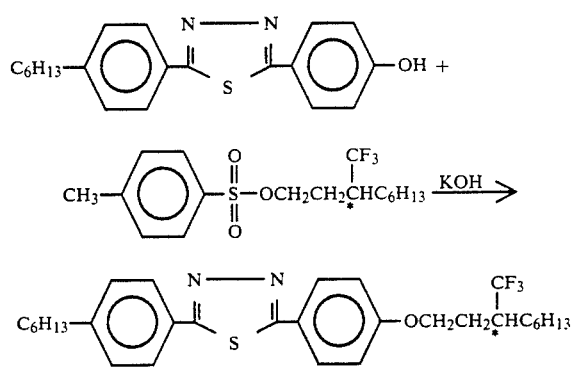

0.27 g of 2-(4-hexylphenyl)-5-(4-hydroxyphenyl)-1, 3, 4-thiadiazole, 0.23 g of p-toluenesulfonic acid-3-trifluoromethylnonyl and 0.063 g of potassium hydroxide were added to butanol, and the mixture was stirred for six hours at 100° C. After the reaction was completed, water was added, ethyl acetate extraction was performed, the solution was dried, the solvent was removed, and the solution was refined by column chromatography (toluene:ethyl acetate=9:1) and recrystallization (toluene/ethanol), so that 0.30 g of a desired material was obtained.

Phase transition temperature (°C.)

$$Cry \overset{76.2}{\rightarrow} S_c* \underset{81.8}{\overset{82.7}{\rightleftarrows}} Iso.$$
$$65.6 \searrow \nearrow 73.0$$
$$S_3$$

EMBODIMENT 6

A liquid crystal composite A which had the liquid crystal compound produced in Embodiment 2 as its component was prepared. Furthermore, a liquid crystal composite B which did not contain the liquid crystal compound in Embodiment 2 was prepared as an example for comparison. The phase transition temperatures of the liquid crystal composites A and B are as follows.

<Liquid crystal composite A>

-continued

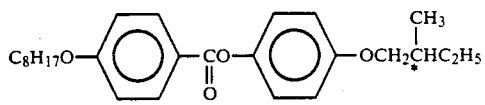
64.0 wt %

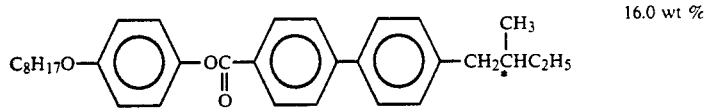
16.0 wt %

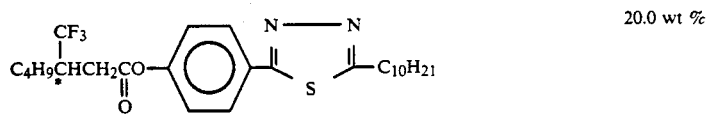
20.0 wt %

<Liquid crystal composite B>

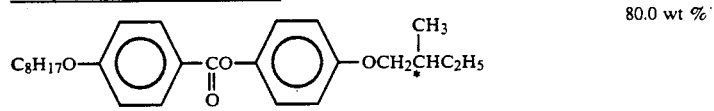
80.0 wt %

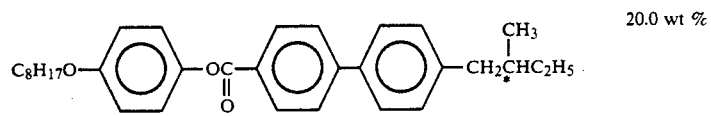
20.0 wt %

Phase transition temperature (°C.)

Liquid crysral composite A $$Cry \xrightleftharpoons{13.0} S_c^* \xrightleftharpoons{47} S_A \xrightleftharpoons{54} Ch \xrightleftharpoons{59} Iso.$$

Liquid crysral composite B $$Cry \xrightleftharpoons{20} S_c^* \xrightleftharpoons{53} S_A \xrightleftharpoons{65} Ch \xrightleftharpoons{76} Iso.$$

Two glass plates having the thickness of 0.7 mm were prepared. An ITO film was formed on each of the glass plates so as to form a voltage applying electrode thereon, and SiO₂ was vacuum-evaporated on the electrode as an insulating layer.

An isopropyl alcohol solution including a silane coupling agent of 0.2% (manufactured by Shin-Etsu Chemical Co., KBM-602) was applied onto the glass plates for fifteen seconds at 2000 r.p.m., and the surfaces of the glass plates were treated. After that, the glass plates were heated and dried for twenty minutes at 120° C.

Furthermore, a dimethylacetamide solution having a polyimide resin precursor (manufactured by Toray Industries, Inc., SP-510) of 2% was applied onto the glass plates with the ITO films, whose surfaces were treated, for fifteen seconds by a spinner having the rotation speed of 2000 r.p.m. After films were formed, the heat condensation calcination treatment was conducted on the glass plates for sixty minutes at 300° C. The thickness of these applied films was approximately 700Å.

After calcination, a rubbing treatment was conducted on the films by acetate flocked cloth, and the films were washed by isopropyl alcohol liquid. After aluminous beads having the average diameter of 2 μm were sprayed onto one of the glass plates, the oriented films composed of polyimide were disposed so that the rubbing treatment axes of the films were parallel with each other. The glass plates were stuck together with an adhesive sealing agent [Lixon Bond (manufactured by Chisso Corp.)], and heated and dried for sixty hours at 100° C., so that a cell was formed.

Then, the ferroelectric liquid crystal composites A and B, which had been previously prepared, were each poured into the formed cell in vacuum, in an isotropic phase and in a state of uniformly mixed liquid. By gradually cooling the isotropic phase at 0.5° C./h, a ferroelectric liquid crystal device was formed.

The measurement by a Berek phase plate revealed that the cell is approximately 2 μm thick.

The response speed (referred to as the optical response speed hereinafter) was measured with this ferroelectric liquid crystal device by detecting the amount Ps of the spontaneous polarization and the optical response (change in the amount of transmitting light:0 to 90%) under a crossed nicol when a voltage whose peak-to-peak voltage Vpp was 20V was applied. The measurement results are as follows:

| temperature | liquid crystal composites | |
|---|---|---|
| | A | B |
| Spontaneous Polarization (nC/cm²) | | |
| 25 | 24.9 | 2.5 |
| 35 | 18.0 | 1.9 |
| 40 | 13.3 | 1.2 |
| Response Speed (μsec) | | |
| 25 | 370 | 1280 |
| 35 | 192 | 690 |
| 40 | 154 | 550 |

The composite A which contains the optically active liquid crystal compound of the present invention has a larger spontaneous polarization and a higher response speed than those of the composite B which does not contain the component. The above results reveal that the use of the optically active liquid crystal compound of the present invention greatly contributed to the improvement of the response property.

EMBODIMENT 7

Similarly, a liquid crystal composite C including the liquid crystal compound produced in Embodiment 1 as its component was prepared.

The phase transition temperature and the spontaneous polarization of the liquid crystal composite C are as follows:

<Liquid Crystal Composite C>

$C_8H_{17}$—[pyrimidine]—[benzene]—$OC_6H_{13}$    46.1 wt %

$C_8H_{17}$—[pyrimidine]—[benzene]—$OC_9H_{19}$    23.0 wt %

$C_{10}H_{21}$—[pyrimidine]—[benzene]—$OC_8H_{17}$    11.5 wt %

$C_3H_7$—[H cyclohexane]—$CO\underset{\|}{\ }O$—[benzene]—[pyrimidine]—$C_{11}H_{23}$    3.6 wt %

$C_4H_9$—[H cyclohexane]—$CO\underset{\|}{\ }O$—[benzene]—[pyrimidine]—$C_{11}H_{23}$    3.6 wt %

$C_5H_{11}$—[H cyclohexane]—$CO\underset{\|}{\ }O$—[benzene]—[pyrimidine]—$C_{11}H_{23}$    7.2 wt %

$C_4H_9\overset{CF_3}{\underset{*}{C}}HCH_2$—[thiadiazole N—N / S]—[benzene]—$OCC_{10}H_{21}\underset{\|}{\ }O$    5.0 wt %

Phase Transition Temperature (°C.)

$Cry \xrightleftharpoons{9.0} S_C^* \xrightleftharpoons{58.2} S_A \xrightleftharpoons{63.4} Ch \xrightleftharpoons{73.8} Iso.$ Spontaneous Polarization (nC/cm²)

| temperature | liquid crystal composite C |
|---|---|
| 10 | 4.6 |
| 30 | 3.4 |
| 45 | 1.8 |

Then, the response time was measured by using the same cell as that in Embodiment 6 in the same manner as in Embodiment 6. The measurement results are as follows:

Response Time (μsec)

| temperature | liquid crystal composite C |
|---|---|
| 10 | 600 |
| 30 | 261 |
| 45 | 156 |

EMBODIMENT 8

Similarly, a liquid crystal composite D including the liquid crystal compound produced in Embodiment 2 as its component was prepared.

The phase transition temperature and the spontaneous polarization of the liquid crystal composite D are as follows:

<Liquid Crystal Composite D>

-continued

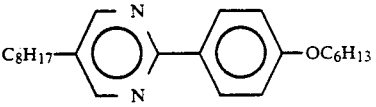 46.1 wt %

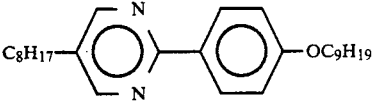 23.0 wt %

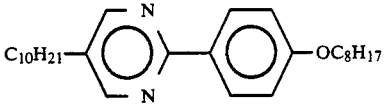 11.5 wt %

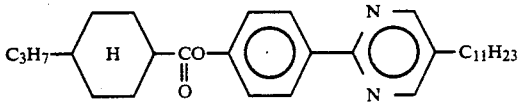 3.6 wt %

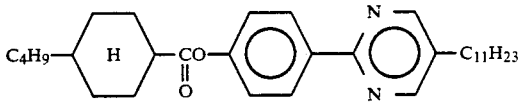 3.6 wt %

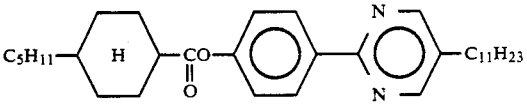 7.2 wt %

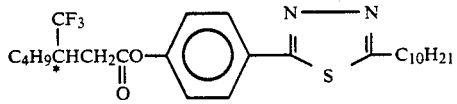 5.0 wt %

Phase Transition Temperature (°C.)

Cry $\xleftrightarrow{7.2}$ S$_c$* $\xleftrightarrow{55.7}$ S$_A$ $\xleftrightarrow{59.7}$ Ch $\xleftrightarrow{72.5}$ Iso.

| Spontaneous Polarization (nC/cm$^2$) | |
|---|---|
| temperature | liquid crystal composite D |
| 10 | 4.0 |
| 30 | 3.5 |
| 45 | 2.2 |

Then, the response time was measured by using the same cell as that in Embodiment 6 in the same manner as in Embodiment 6. The measurement results are as follows:

| Response Time (μsec) | |
|---|---|
| temperature | liquid crystal composite D |
| 10 | 640 |
| 30 | 294 |
| 45 | 189 |

EMBODIMENT 9

Similarly, a liquid crystal composite E including the liquid crystal compound produced in Embodiment 3 as its component was prepared.

The phase transition temperature and the spontaneous polarization of the liquid crystal composite E are as follows:

<Liquid Crystal Composite E>

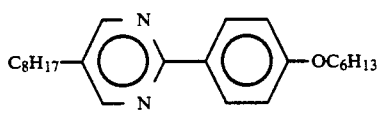 46.1 wt %

-continued

C$_8$H$_{17}$—[pyrimidine]—[phenyl]—OC$_9$H$_{19}$  23.0 wt %

C$_{10}$H$_{21}$—[pyrimidine]—[phenyl]—OC$_8$H$_{17}$  11.5 wt %

C$_3$H$_7$—[H cyclohexyl]—CO-O—[phenyl]—[pyrimidine]—C$_{11}$H$_{23}$  3.6 wt %

C$_4$H$_9$—[H cyclohexyl]—CO-O—[phenyl]—[pyrimidine]—C$_{11}$H$_{23}$  3.6 wt %

C$_5$H$_{11}$—[H cyclohexyl]—CO-O—[phenyl]—[pyrimidine]—C$_{11}$H$_{23}$  7.2 wt %

CF$_3$ | C$_6$H$_{13}$CHCH$_2$CH$_2$O—[phenyl]—[thiadiazole]—C$_{10}$H$_{21}$  5.0 wt %

Phase Transition Temperature (°C.)

Cry $\xleftrightarrow{8.1}$ S$_c^*$ $\xleftrightarrow{54.8}$ S$_A$ $\xleftrightarrow{58.6}$ Ch $\xleftrightarrow{72.7}$ Iso.

| Spontaneous Polarization (nC/cm$^2$) | |
|---|---|
| temperature | liquid crystal composite E |
| 10 | 4.0 |
| 30 | 3.0 |
| 45 | 2.0 |

Then, the response time was measured by using the same cell as that in Embodiment 6 in the same manner as in Embodiment 6. The measurement results are as follows:

| Response Time (μsec) | |
|---|---|
| temperature | liquid crystal composite E |
| 10 | 625 |
| 30 | 288 |
| 45 | 174 |

EMBODIMENT 10

Similarly, a liquid crystal composite F including the liquid crystal compound produced in Embodiment 4 as its component was prepared.

The phase transition temperature and the spontaneous polarization of the liquid crystal composite F are as follows:

<Liquid Crystal Composite F>

C$_8$H$_{17}$—[pyrimidine]—[phenyl]—OC$_6$H$_{13}$  54.3 wt %

C$_8$H$_{17}$—[pyrimidine]—[phenyl]—OC$_9$H$_{19}$  27.1 wt %

-continued

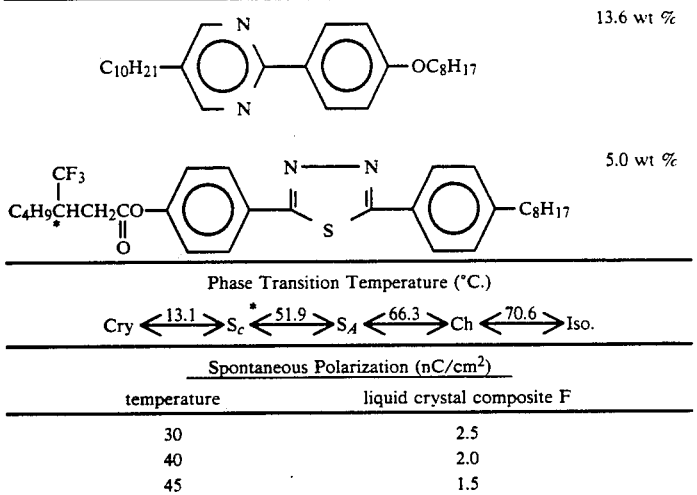

| | 13.6 wt % |
| | 5.0 wt % |

Phase Transition Temperature (°C.)

Cry $\xleftarrow{13.1}$ S$_c^*$ $\xleftarrow{51.9}$ S$_A$ $\xleftarrow{66.3}$ Ch $\xleftarrow{70.6}$ Iso.

Spontaneous Polarization (nC/cm$^2$)

| temperature | liquid crystal composite F |
|---|---|
| 30 | 2.5 |
| 40 | 2.0 |
| 45 | 1.5 |

Then, the response time was measured by using the same cell as that in Embodiment 6 in the same manner as in Embodiment 6. The measurement results are as follows:

Response Time (μsec)

| temperature | liquid crystal composite F |
|---|---|
| 30 | 227 |
| 40 | 148 |
| 45 | 93 |

EMBODIMENT 11

Similarly, a liquid crystal composite G including the liquid crystal compound produced in Embodiment 5 as its component was prepared.

The phase transition temperature and the spontaneous polarization of the liquid crystal composite G are as follows:

<Liquid Crystal Composite G>

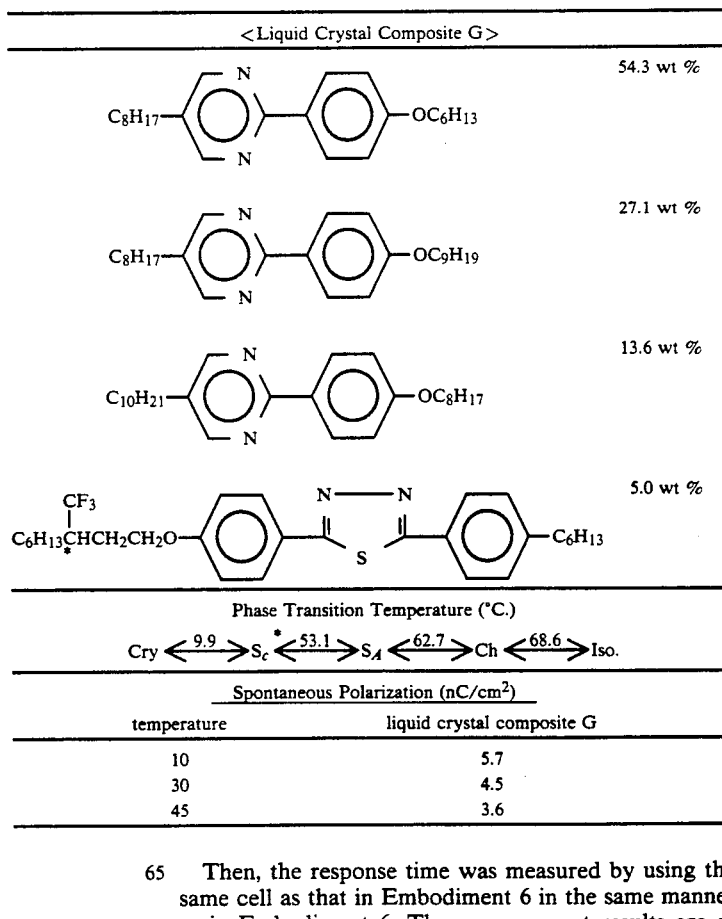

| | 54.3 wt % |
| | 27.1 wt % |
| | 13.6 wt % |
| | 5.0 wt % |

Phase Transition Temperature (°C.)

Cry $\xrightarrow{9.9}$ S$_c^*$ $\xrightarrow{53.1}$ S$_A$ $\xrightarrow{62.7}$ Ch $\xrightarrow{68.6}$ Iso.

Spontaneous Polarization (nC/cm$^2$)

| temperature | liquid crystal composite G |
|---|---|
| 10 | 5.7 |
| 30 | 4.5 |
| 45 | 3.6 |

Then, the response time was measured by using the same cell as that in Embodiment 6 in the same manner as in Embodiment 6. The measurement results are as follows:

| Response Time (μsec) | |
| --- | --- |
| temperature | liquid crystal composite G |
| 10 | 550 |
| 30 | 202 |
| 45 | 96 |

As described above, a liquid crystal composite having a high optical response speed could be obtained by using the compound of the present invention.

EMBODIMENT 12

A film was formed by applying a polyimide resin precursor (manufactured by Toray Industries, Inc., SP-510) onto each of two glass plates, on which an ITO (Indium Tin Oxide) film was formed as a transparent electrode, by a spinner, and made into a polyimide film by being calcined for sixty minutes at 300° C. Subsequently, an alignment treatment was conducted on the films by rubbing, and a cell was produced so that rubbing treatment axes of the films were orthogonal to each other (the cell is 8 μm thick), and by pouring a nematic liquid crystal composite [Lixon GR-63: a biphenyl liquid crystal mixture manufactured by Chisso Corp.], a TN (Twisted Nematic) cell was obtained The observation of the cell by a polarizing microscope revealed that reverse domain (stripes) was caused.

When a liquid crystal mixture, in which the liquid crystal compound (1% in weight) shown in Embodiment 1 of the present invention was added to the above Lixon GR-63 (99% in weight), was made into a TN cell and observed in the same manner as above, reverse domain was not found and the TN cell was a uniform nematic phase. This revealed that the liquid crystal compound of the present invention was effective to prevent reverse domain from arising.

According to the present invention, a liquid crystal compound which has an excellent electric field responsibility can be obtained. Furthermore, it can be confirmed that a liquid crystal composite and a liquid crystal device containing the liquid crystal compound are effective to prevent reverse domain from arising as well as to improve the response speed.

While the present invention has been described with respect to what is presently considered to be the preferred embodiments, it is to be understood that the invention is not limited to the disclosed embodiments. The present invention is intended to cover various modifications and equivalent arrangements included within the spirit and scope of the appended claims.

What is claimed is:

1. A liquid crystal compound represented by the following general formula (I):

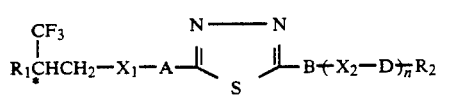

wherein $R_1$ is a straight chain alkyl having 1-12 carbon atoms, $R_2$ is a straight chain or branched chain alkyl having 1~18 carbon atoms and in which one or more than two methylene, not adjoining, may be substituted by —Y—,

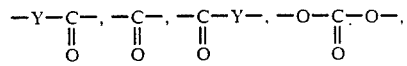

—CH=CH— or —C≡C—. Y is O or S, A is —$A_1$— or —$A_1$—$A_2$—, B is —$B_1$— or —$B_1$—$B_2$—, and $A_1$, $A_2$, $B_1$ and $B_2$ each is selected from

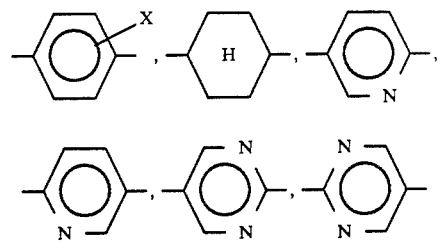

and a single bond. Z is a hydrogen, halogen, cyano or methyl, $X_1$ is a single bond when A is a single bond and is —$CH_2O$—,

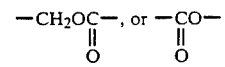

when A is not a single bond, n is 0 or 1, $X_2$ is

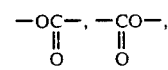

—$OCH_2$—, or —$CH_2O$, D is

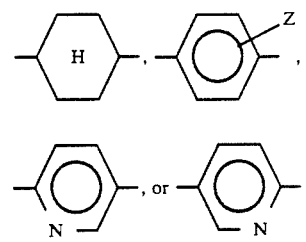

and * designates an asymmetric carbon atom.

2. A liquid crystal compound according to claim 1, wherein $R_2$ is selected from the following (i) to (iii):
   i) a n-alkyl having 1 to 18 carbon atoms, and more preferably, 3 to 12 carbon atoms;
   ii) a branched chain alkyl having the formula

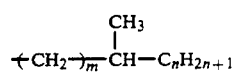

wherein m is one of integers of 0 to 7, n is one of integers of 2 to 9; and
   iii) an alkyl ether having the formula

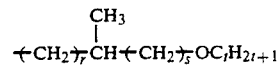

wherein r is one of integers of 0 to 7, s is 0 or 1, t is one of integers of 1 to 14.

3. A liquid crystal compound according to claim 2, wherein said branched chain alkyl is optically active.

4. A liquid crystal compound according to claim 2, wherein said alkyl ether is optically active.

5. A liquid crystal compound according to claim 1, wherein when —A— is —A₁— in the general formula (I), and —A₁— is selected from a single bond,

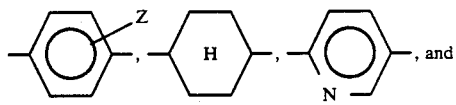, and

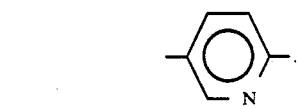

6. A liquid crystal compound according to claim 5, wherein —A₁— is selected from a single bond,

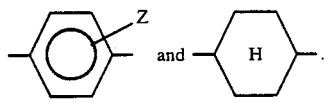

7. A liquid crystal compound according to claim 5, wherein when —A₁— is a single bond, and —B— is selected from

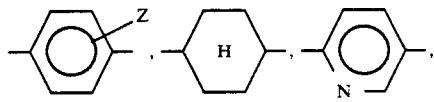

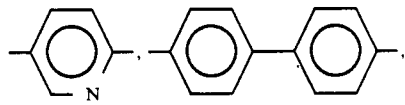

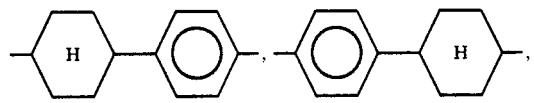

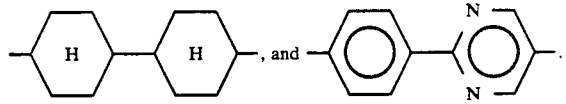

8. A liquid crystal compound according to claim 5, wherein when —A₁— is selected from

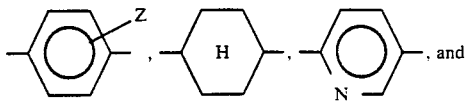

—B— is —B₁— and —B₁— is selected from a single bond,

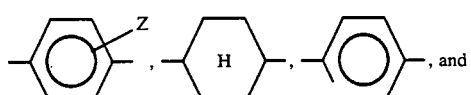

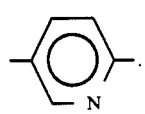

9. A liquid crystal compound according to claim 8, wherein —B₁— is selected from a single bond,

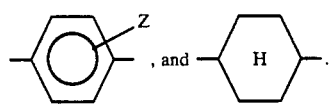

10. A liquid crystal compound according to claim 1, wherein when —A— is —A₁—A₂— in the general formula (I), and —A₁—A₂— is selected from

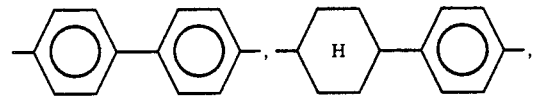

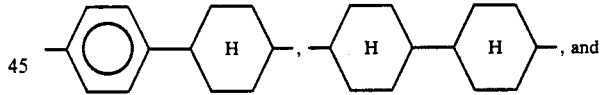

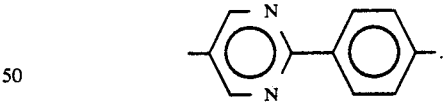

11. A liquid crystal compound according to claim 10, wherein when —A— is —A₁—A₂—, and —B— is a single bond.

12. A liquid crystal compound according to claim 1, having a structure represented by one of the following formulas (1-1) to (1-110):

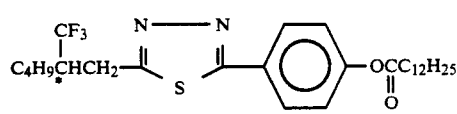 (1-1)

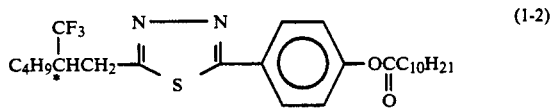 (1-2)

$$\underset{\text{C}_4\text{H}_9\overset{*}{\text{C}}\text{HCH}_2}{\overset{\text{CF}_3}{|}}\underset{\text{S}}{\overset{\text{N}}{\diagdown}}\underset{}{\overset{\text{N}}{\diagup}}\text{—}\!\!\bigcirc\!\!\text{—OCC}_{11}\text{H}_{23} \atop \phantom{xxxxxxxxxxxxxxxx}\overset{}{\underset{\text{O}}{\|}}$$ (1-3)

$$\underset{\text{C}_4\text{H}_9\overset{*}{\text{C}}\text{HCH}_2}{\overset{\text{CF}_3}{|}}\underset{\text{S}}{\overset{\text{N}—\text{N}}{\diagdown\diagup}}\text{—}\!\!\bigcirc\!\!\text{—OCC}_{8}\text{H}_{17} \atop \phantom{xxxxxxxxxxxxxx}\overset{}{\underset{\text{O}}{\|}}$$ (1-4)

(1-5) C₆H₁₃C*HCH₂—[thiadiazole]—⌬—OCC₇H₁₅(=O)

(1-6) C₈H₁₇C*HCH₂—[thiadiazole]—⌬—OCC₄H₉(=O)

(1-7) C₆H₁₃C*HCH₂—[thiadiazole]—⌬—OCC₁₀H₂₁(=O)

(1-8) C₃H₇C*HCH₂—[thiadiazole]—⌬—OCC₁₁H₂₃(=O)

(1-9) CH₃C*HCH₂—[thiadiazole]—⌬—OCC₁₄H₂₉(=O)

(1-10) C₄H₉C*HCH₂—[thiadiazole]—⌬—OC₁₂H₂₅

(1-11) C₄H₉C*HCH₂—[thiadiazole]—⌬—OC₇H₁₅

(1-12) C₄H₉C*HCH₂—[thiadiazole]—⌬—OC₁₀H₂₁

(1-13) C₄H₉C*HCH₂—[thiadiazole]—⌬—OC₉H₁₉

(1-14) C₄H₉C*HCH₂—[thiadiazole]—⌬—OC₈H₁₇

(1-15) C₆H₁₃C*HCH₂—[thiadiazole]—⌬—OC₁₀H₂₁

(1-16) C₆H₁₃C*HCH₂—[thiadiazole]—⌬—OC₇H₁₅

(1-17) C₃H₉C*HCH₂—[thiadiazole]—⌬—OC₁₂H₂₅

(1-18) C₄H₉C*HCH₂—[thiadiazole]—⌬—C₁₂H₂₅

(1-19) C₄H₉C*HCH₂—[thiadiazole]—⌬—C₁₀H₂₁

(1-20) C₆H₁₃C*HCH₂—[thiadiazole]—⌬—C₉H₁₉

(1-21) C₃H₇C*HCH₂—[thiadiazole]—⌬—C₅H₁₁

(1-22) C₄H₉C*HCH₂—[thiadiazole]—⌬(F)—OCC₁₀H₂₁(=O)

(1-23) C₈H₁₇C*HCH₂—[thiadiazole]—⌬(F)—OC₈H₁₇

(1-24) C₃H₇C*HCH₂—[thiadiazole]—⌬(F)—C₁₂H₂₅

(1-25) C₆H₁₃C*HCH₂—[thiadiazole]—⌬—OCOC₁₀H₂₁(=O)

(1-26) C₄H₉C*HCH₂—[thiadiazole]—⌬—O—CH₂—C*H(CH₃)C₂H₅

Note: All structures above contain the 1,3,4-thiadiazole ring (N=N / S) connecting the chiral alkyl chain (left) to a para-substituted phenyl ring (right). The asterisk (*) denotes a chiral carbon.

$$C_8H_{17}\overset{CF_3}{\underset{*}{C}}HCH_2-\underset{S}{\overset{N=N}{\diagup\!\!\!\diagdown}}-\underset{}{\bigcirc}-O-\underset{O}{\overset{CH_3}{\underset{}{C}}}-\overset{*}{C}HOC_3H_7 \quad (1\text{-}27)$$

$$C_4H_9\overset{CF_3}{\underset{*}{C}}HCH_2-\underset{S}{\overset{N=N}{\diagup\!\!\!\diagdown}}-\bigcirc-O(CH_2)_{\overline{15}}CH=CH_2 \quad (1\text{-}28)$$

$$C_5H_{11}\overset{CF_3}{\underset{*}{C}}HCH_2-\underset{S}{\overset{N-N}{\diagup\!\!\!\diagdown}}-\bigcirc-\underset{O}{\overset{}{O}}CC_{10}H_{21} \quad (1\text{-}29)$$

$$C_7H_{15}\overset{CF_3}{\underset{*}{C}}HCH_2-\underset{S}{\overset{N-N}{\diagup\!\!\!\diagdown}}-\bigcirc-OC_{12}H_{25} \quad (1\text{-}30)$$

$$C_4H_9\overset{CF_3}{\underset{*}{C}}HCH_2-\underset{S}{\overset{N-N}{\diagup\!\!\!\diagdown}}-\bigcirc-OCH_2CH_2-S-C_3H_7 \quad (1\text{-}31)$$

$$C_6H_{13}\overset{CF_3}{\underset{*}{C}}HCH_2-\underset{S}{\overset{N-N}{\diagup\!\!\!\diagdown}}-\bigcirc-\underset{O}{\overset{}{O}}CCH_2-S-C_2H_5 \quad (1\text{-}32)$$

$$C_4H_9\overset{CF_3}{\underset{*}{C}}HCH_2-\underset{S}{\overset{N-N}{\diagup\!\!\!\diagdown}}-\bigcirc-\bigcirc-OC_{10}H_{21} \quad (1\text{-}33)$$

$$C_4H_9\overset{CF_3}{\underset{*}{C}}HCH_2-\underset{S}{\overset{N-N}{\diagup\!\!\!\diagdown}}-\bigcirc-\bigcirc-OC_8H_{17} \quad (1\text{-}34)$$

$$C_4H_9\overset{CF_3}{\underset{*}{C}}HCH_2-\underset{S}{\overset{N-N}{\diagup\!\!\!\diagdown}}-\bigcirc-\bigcirc-OC_9H_{19} \quad (1\text{-}35)$$

$$C_6H_{13}\overset{CF_3}{\underset{*}{C}}HCH_2-\underset{S}{\overset{N-N}{\diagup\!\!\!\diagdown}}-\bigcirc-\bigcirc-OC_6H_{13} \quad (1\text{-}36)$$

$$C_4H_9\overset{CF_3}{\underset{*}{C}}HCH_2-\underset{S}{\overset{N-N}{\diagup\!\!\!\diagdown}}-\bigcirc-\bigcirc-\underset{O}{\overset{}{O}}CC_8H_{17} \quad (1\text{-}37)$$

$$C_8H_{17}\overset{CF_3}{\underset{*}{C}}HCH_2-\underset{S}{\overset{N-N}{\diagup\!\!\!\diagdown}}-\bigcirc-\bigcirc-\underset{O}{\overset{}{O}}CC_7H_{15} \quad (1\text{-}38)$$

$$C_3H_7\overset{CF_3}{\underset{*}{C}}HCH_2-\underset{S}{\overset{N-N}{\diagup\!\!\!\diagdown}}-\bigcirc-\bigcirc-C_6H_{13} \quad (1\text{-}39)$$

$$C_4H_9\overset{CF_3}{\underset{*}{C}}HCH_2-\underset{S}{\overset{N-N}{\diagup\!\!\!\diagdown}}-\bigcirc-\bigcirc-OC_{10}H_{21} \quad (1\text{-}40)$$

-continued (1-41)

(1-42)

(1-43)

(1-44)

(1-45)

(1-46)

(1-47)

(1-48)

(1-49)

(1-50)

(1-51)

(1-52)

(1-53)

(1-54)

(1-55)

(1-56)

(1-57)

(1-58)

-continued
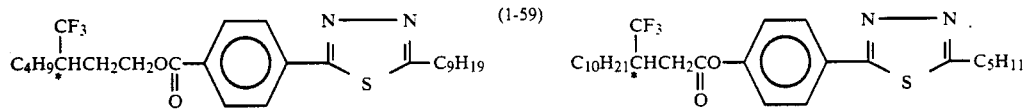
(1-59) (1-60)
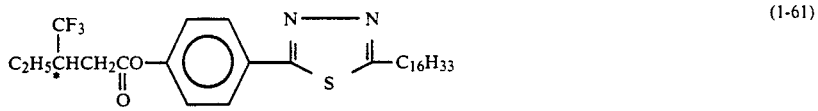
(1-61)
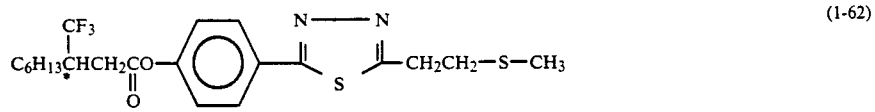
(1-62)
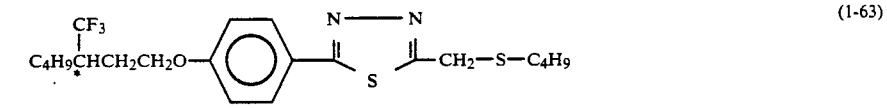
(1-63)
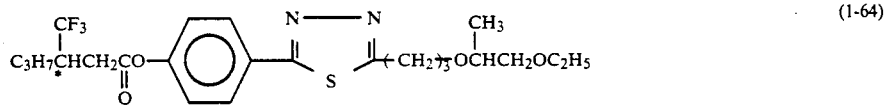
(1-64)
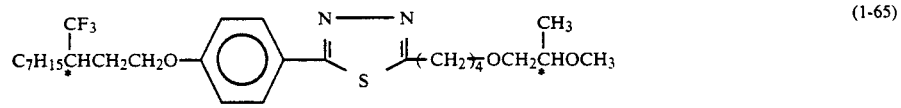
(1-65)
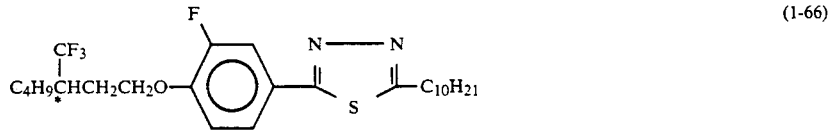
(1-66)
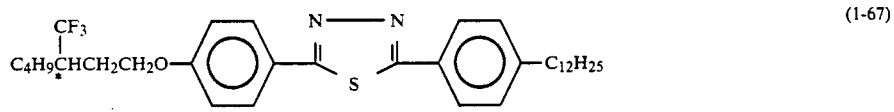
(1-67)
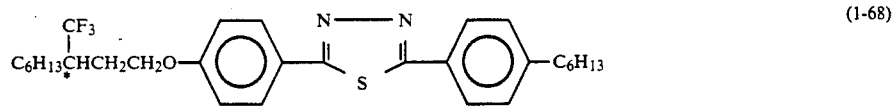
(1-68)
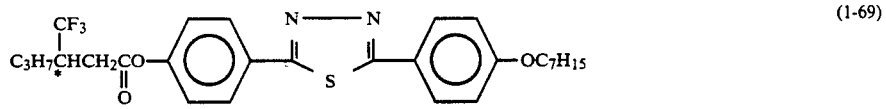
(1-69)
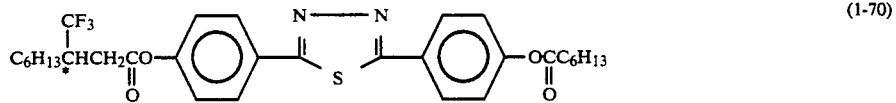
(1-70)
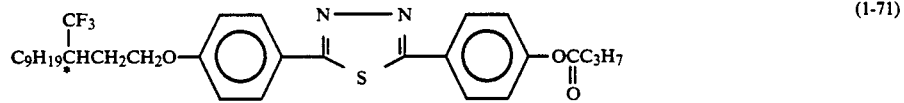
(1-71)
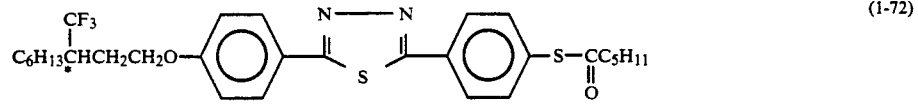
(1-72)

-continued
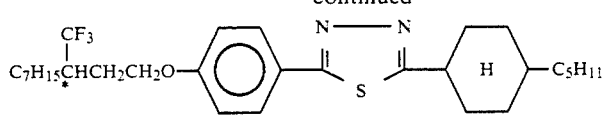 (1-73)
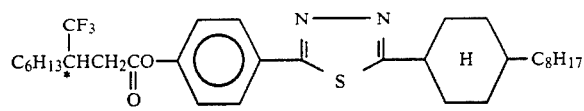 (1-74)
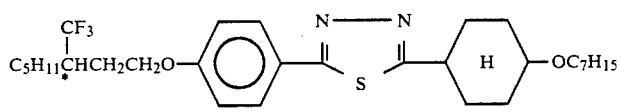 (1-75)
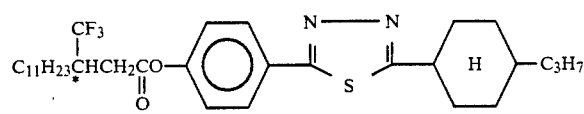 (1-76)
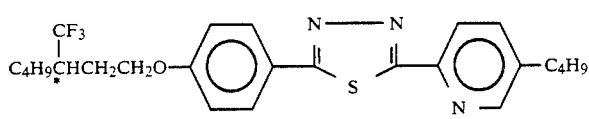 (1-77)
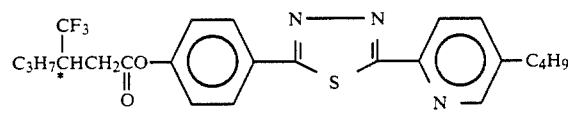 (1-78)
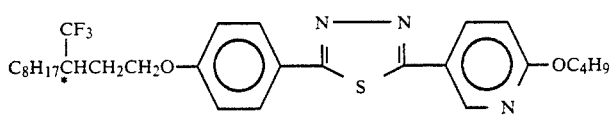 (1-79)
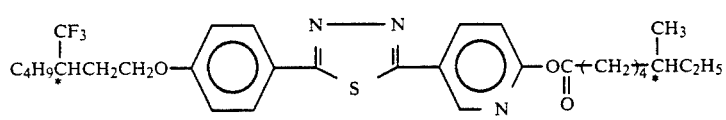 (1-80)
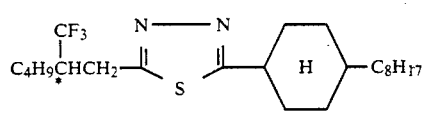 (1-81)  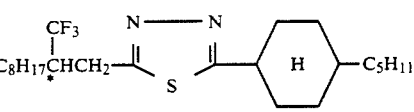 (1-82)
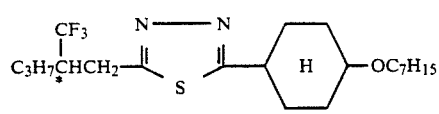 (1-83)  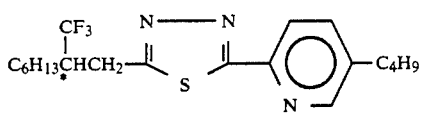 (1-84)
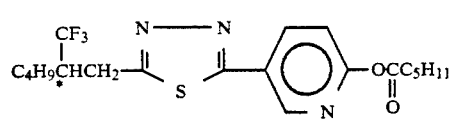 (1-85)  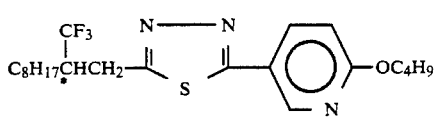 (1-86)
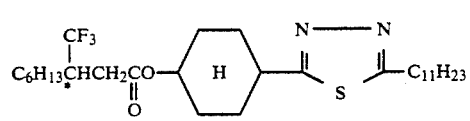 (1-87)  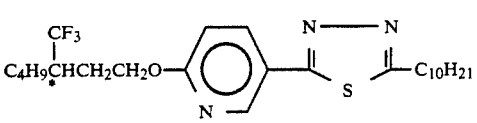 (1-88)
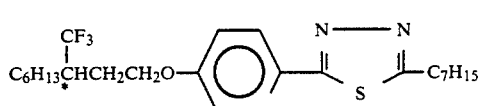 (1-89)

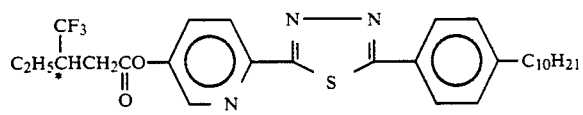 (1-90)
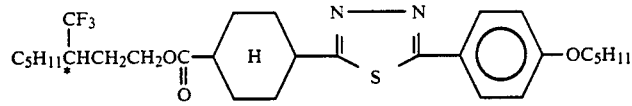 (1-91)
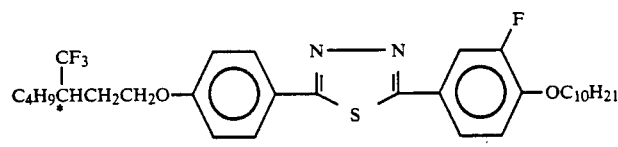 (1-92)
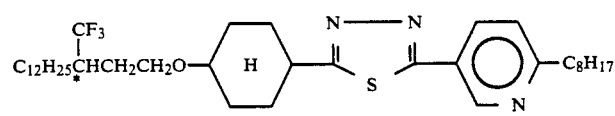 (1-93)
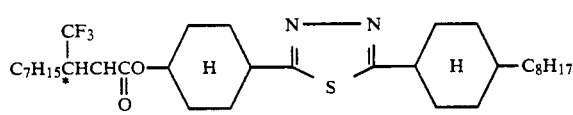 (1-94)
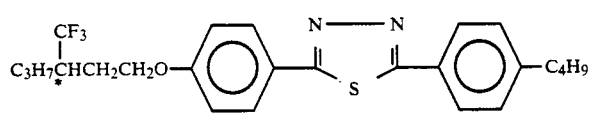 (1-95)
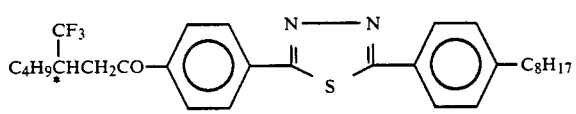 (1-96)
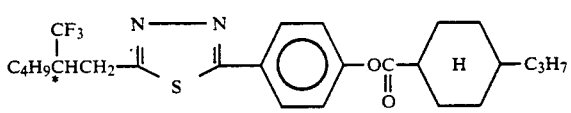 (1-97)
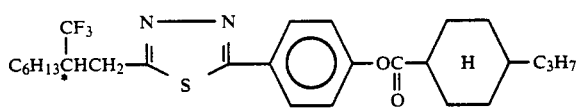 (1-98)
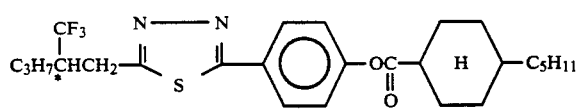 (1-99)
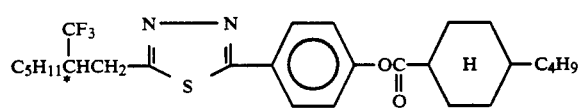 (1-100)
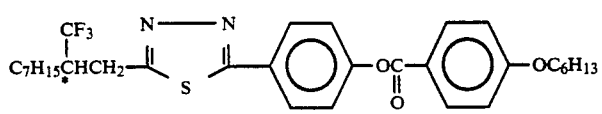 (1-101)
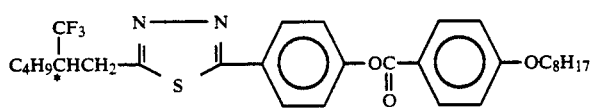 (1-102)

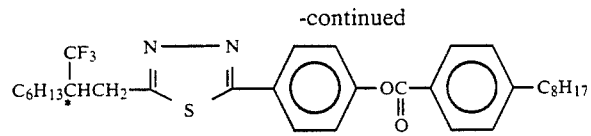 (1-103)

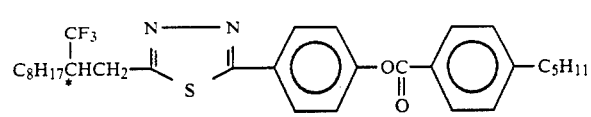 (1-104)

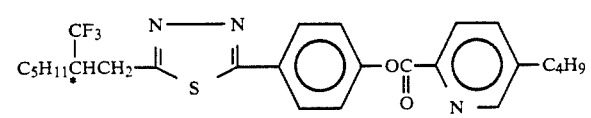 (1-105)

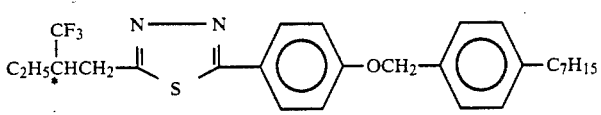 (1-106)

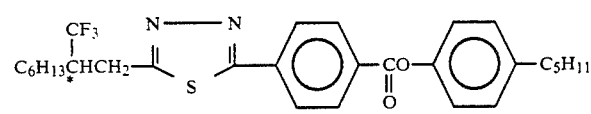 (1-107)

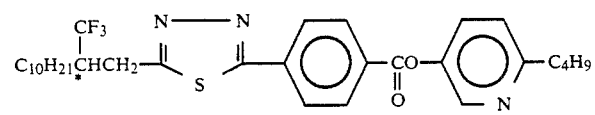 (1-108)

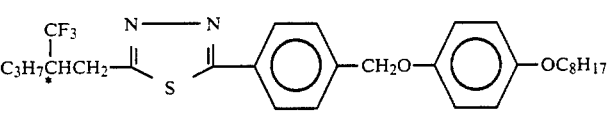 (1-109)

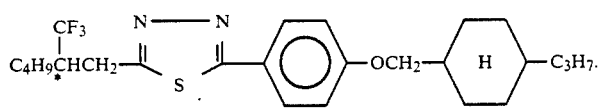 (1-110)

13. A liquid crystal composite comprising a liquid crystal compound according to claim 1 and at least one liquid crystal compound other than said compound of claim 1.

14. A liquid crystal composite according to claim 13, wherein said one or more liquid crystal compound other than the compound of claim 1 is selected from compounds having chiral smectic phases and non-chiral smectic liquid crystal compounds, and said liquid crystal composite having a chiral smectic phase.

15. A liquid crystal composite according to claim 13, wherein said compound represented by the general formula (I) forms 0.1% to 99% by weight based on the total weight of said liquid crystal composite having a chiral smectic phase.

16. A liquid crystal composite according to claim 13, wherein said compound represented by the general formula (I) forms 1% to 90% by weight based on the total weight of said liquid crystal compound having a chiral smectic phase.

17. A liquid crystal device including a liquid crystal composite according to claim 13 disposed between a pair of electrode substrates.

18. A liquid crystal device according to claim 17, wherein alignment films are formed on said pair of electrode substrates.

19. A liquid crystal composite including a nematic liquid crystal and a liquid crystal compound according to claim 1, said liquid crystal compound forming 0.01% to 50% by weight based on the total weight of said liquid crystal composite.

20. A liquid crystal device including a liquid crystal composite according to claim 19 disposed between a pair of electrode substrates.

21. A liquid crystal composite including a nematic liquid crystal or a chiral nematic liquid crystal, and a liquid crystal compound according to claim 1, said liquid crystal compound forming 0.01% to 80% by weight based on the total weight of said liquid crystal composite.

22. A liquid crystal device including a liquid crystal composite according to claim 21 disposed between a pair of electrode substrates.

* * * * *

UNITED STATES PATENT AND TRADEMARK OFFICE
CERTIFICATE OF CORRECTION

PATENT NO. : 5,098,600
DATED : March 24, 1992
INVENTOR(S) : SHINICHI NAKAMURA, ET AL.

Page 1 of 3

It is certified that error appears in the above-identified patent and that said Letters Patent is hereby corrected as shown below:

Item (57) ABSTRACT

Column 2, line 13, "—C|C—." should read -- —C≡C—. --.
Column 2, line 15, "is" should read --are--.

Column 2, lines 17-21, "  " should read  .

Column 2, line 37, "n is 0 or 1," should read --n is 0 or 1, $X_2$ is--.

COLUMN 2

Line 26, "(ScC*" should read --(SmC*--.

COLUMN 3

Line 57, " 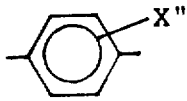 " should read 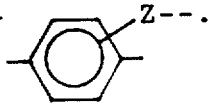 .

COLUMN 4

Line 54, "—A—," should read -- —$A_1$—, --.

COLUMN 6

Line 63, "by" should read --by —O—, --.

UNITED STATES PATENT AND TRADEMARK OFFICE
CERTIFICATE OF CORRECTION

PATENT NO. : 5,098,600
DATED : March 24, 1992
INVENTOR(S) : SHINICHI NAKAMURA, ET AL.

It is certified that error appears in the above-identified patent and that said Letters Patent is hereby corrected as shown below:

COLUMN 19

Line 30, "
$$\begin{array}{c} CH_3 \\ | \\ \underset{*}{C}H_2H_5 \end{array}$$
" should read --
$$\begin{array}{c} CH_3 \\ | \\ \underset{*}{C}HC_2H_5 \end{array}$$
--.

COLUMN 51

Line 66, "1~18" should read --1-18--.

COLUMN 52

Line 8, "is" should read --are--.

Line 12, " X" should read -- Z--.

Line 21, "a" should be deleted.

COLUMN 53

Line 6, "when" should be deleted.
Line 29, "when" should be deleted.
Line 54, "when" should be deleted.

COLUMN 54

Line 34, "when" should be deleted.
Line 54, "when" should be deleted.

UNITED STATES PATENT AND TRADEMARK OFFICE
CERTIFICATE OF CORRECTION

PATENT NO. : 5,098,600

DATED : March 24, 1992

INVENTOR(S) : SHINICHI NAKAMURA, ET AL.

It is certified that error appears in the above-identified patent and that said Letters Patent is hereby corrected as shown below:

<u>COLUMN 67</u>

Line 64, "compound" should read --composite--.

Signed and Sealed this

Twenty-first Day of December, 1993

Attest:

BRUCE LEHMAN

Attesting Officer     Commissioner of Patents and Trademarks